United States Patent
Dillon et al.

(10) Patent No.: US 10,561,620 B2
(45) Date of Patent: Feb. 18, 2020

(54) COILED TUBE EMULSIFICATION SYSTEMS

(71) Applicant: Rezolute, Inc., Redwood City, CA (US)

(72) Inventors: Isaac J. Dillon, Aurora, CO (US); Kathleen M. Campbell, Firestone, CO (US); Sankaram Mantripragada, Windsor, CO (US)

(73) Assignee: Rezolute, Inc., Redwood City, CA (US)

( * ) Notice: Subject to any disclaimer, the term of this patent is extended or adjusted under 35 U.S.C. 154(b) by 139 days.

(21) Appl. No.: 15/705,818

(22) Filed: Sep. 15, 2017

(65) Prior Publication Data

US 2019/0083412 A1  Mar. 21, 2019

(51) Int. Cl.
| | |
|---|---|
| *B01J 13/00* | (2006.01) |
| *B01F 13/00* | (2006.01) |
| *A61K 9/50* | (2006.01) |
| *B01J 13/04* | (2006.01) |
| *B01F 3/08* | (2006.01) |

(52) U.S. Cl.
CPC ............ *A61K 9/5052* (2013.01); *B01F 3/088* (2013.01); *B01F 3/0811* (2013.01); *B01F 3/0861* (2013.01); *B01F 13/0052* (2013.01); *B01J 13/046* (2013.01); *B01F 2003/0834* (2013.01); *B01F 2003/0842* (2013.01)

(58) Field of Classification Search
CPC .... B01F 3/2261; B01F 5/0647; B01F 3/0811; B01F 3/0861; B01F 3/088; B01F 13/0052; B01F 2003/0834; B01F 2003/0842; A61K 9/5052; B01J 13/046
See application file for complete search history.

(56) References Cited

U.S. PATENT DOCUMENTS

| | | | |
|---|---|---|---|
| 3,592,768 A | 7/1971 | Parker | |
| 2005/0227264 A1 | 10/2005 | Nobile et al. | |
| 2009/0255601 A1* | 10/2009 | Baeuerle | B01F 5/061 |
| | | | 137/892 |
| 2011/0150703 A1* | 6/2011 | Castro | B01F 5/061 |
| | | | 422/68.1 |
| 2014/0260993 A1 | 9/2014 | Elms et al. | |
| 2015/0131405 A1* | 5/2015 | Zhou | B01F 5/0647 |
| | | | 366/144 |

FOREIGN PATENT DOCUMENTS

KR   10-0718676 B1   5/2007

* cited by examiner

*Primary Examiner* — Anshu Bhatia
(74) *Attorney, Agent, or Firm* — Kilpatrick Townsend & Stockton LLP

(57) ABSTRACT

Embodiments of the present technology may include a system for forming an emulsion. The system may include a coiled tube. The coiled tube may have a first end and a second end. The second end may be located at a position higher than the position of the first end. The system may also include a plurality of beads disposed within the coiled tube. The system may further include a first inlet fluidly connected to the coiled tube. The first inlet may be configured to deliver a first fluid to the first end before the second end. In addition, the system may include a second inlet fluidly connected to the coiled tube. The second inlet may be configured to deliver a second fluid to the first end before the second end.

30 Claims, 7 Drawing Sheets

COILED TUBE EMULSIFICATION SYSTEMS

BACKGROUND

Biodegradable microparticles may be used to deliver physiologically active substances such as, small molecule drugs, hormones, proteins, diagnostics, and other medically active agents to a patient. Microparticles are suspended in an aqueous diluent to make a suspension, which can be injected parenterally through a needle. They may also be implanted as a solid. After injection, the microparticles degrade and gradually release agents to the body. Biodegradable microparticles may reduce the frequency of injections, as the physiologically active substance is released gradually into the body. The microparticle size distribution affects the required gauge and other characteristics of the needle. More flowable microparticles may be easier to fill into vials and may be more easily injected with a large gauge (smaller diameter) needle. Once in the body, the rate of release and the concentration of the physiologically active substance may be related to the microparticle size, the microparticle size distribution, the initial concentration of the physiologically active substance, and other characteristics of the microparticles. Such biodegradable microparticles also need to meet health and safety regulations for contaminant concentrations including the solvents used to prepare the microparticles. Thus, a need for microparticles with superior syringability, injectability, flowability, uniformity, and purity characteristics exists. Forming microparticles involves forming an emulsion from an oil component and an aqueous component. The process for forming an emulsion can affect the characteristics of the microparticles, and the efficiency of the emulsion forming process may impact the availability and acceptability of microparticles with physiologically active substances. Further, there is a need for a process for the production of microparticles that requires less space than conventional processes. The methods and systems described herein provide solutions to these and other needs.

BRIEF SUMMARY

Embodiments of the present technology may allow for forming an emulsion efficiently and with high homogeneity. Embodiments may use a configuration for mixing an oil phase and an aqueous phase that reduces unwanted chaotic mixing, using laminar flow, which allows for a gentle mixing of components. The configuration used is a coiled or helical tube packed with beads, with the flow directed against the direction of gravity. In addition, the helical or coiled configuration may reduce the footprint of emulsifiers. Several coiled tubes may be nested together in the same or similar space as one coiled tube. As a result, embodiments may include a more efficient and economical process of forming an emulsion. In addition, embodiments of the present technology may produce a targeted distribution of microparticles from the emulsion. Microparticles may be classified by a plurality of screens with recirculating flow from a stirred tank, which may better control the microparticles produced.

Embodiments of the present technology may include a system for forming an emulsion. The system may include a coiled tube. The coiled tube may have a first end and a second end. The second end may be located at a position higher than the position of the first end. The system may also include a plurality of beads disposed within the coiled tube. The system may further include a first inlet fluidly connected to the coiled tube. The first inlet may be configured to deliver a first fluid to the first end before the second end. In addition, the system may include a second inlet fluidly connected to the coiled tube. The second inlet may be configured to deliver a second fluid to the first end before the second end.

Embodiments of the present technology may include a system for forming microparticles from the emulsion by removing the solvent and the water. Microparticles may be prepared by a single emulsification process or a double emulsification process. In the single emulsification process, an organic solvent phase containing a biodegradable polymer, an aqueous solution containing an emulsifier, such as polyvinyl alcohol, and a physiologically active substance may be homogenized to produce an emulsion. The solvent may be evaporated, and water from the resulting hardened microspheres may be removed by air-drying or freeze-drying. In the double emulsification process, an aqueous solution that may contain a physiologically active substance and an organic solvent phase containing a biodegradable polymer may be homogenized to form an emulsion. The emulsion may be mixed with another aqueous solution, which contains an emulsifier such as polyvinyl alcohol. Evaporation of the solvent and water may produce microspheres. When a physiologically active substance is soluble in the organic solvent phase, the method may be single emulsification because it may produce uniform mixing of the biodegradable molecules and the physiologically active substance molecules. When the physiologically active substance is not soluble in the organic solvent phase and is soluble in the aqueous solution, the method may be double emulsification.

Embodiments of the present technology may also include a system for forming an emulsion. The system may include coiled tubes nested together. The system may include a plurality of coiled tubes. For each tube of the plurality of coiled tubes, the coiled tube may include a first end and a second end. The second end may be disposed at a position higher than the position of the first end. For each coiled tube, a first inlet may be fluidly connected to the coiled tube, where the first inlet is configured to deliver a first fluid to the first end before the second end. The system may further include a second inlet. Also for each coiled tube, a second inlet may be fluidly connected to the coiled tube, where the second inlet is configured to deliver a second fluid to the first end before the second end. A plurality of beads may be disposed within the coiled tubes. Each coiled tube may be coiled around a longitudinal axis. Each coiled tube may be characterized by a first width in a direction perpendicular to the longitudinal axis. The plurality of coiled tubes may be coaxial with the longitudinal axis. In addition, the plurality of coiled tubes may be characterized by a second width in a direction perpendicular to the longitudinal axis. The first width may equal the second width.

Embodiments of the present technology may include a method of forming an emulsion. The method may include flowing an oil stream and an aqueous stream into a coiled tube to form a mixture of an oil phase and an aqueous phase in the coiled tube. The method may also include flowing the mixture in the coiled tube against gravity and under laminar conditions. A plurality of beads may be disposed within the coiled tube. The method may further include mixing the oil phase and the aqueous phase in the coiled tube until the emulsion is formed.

A better understanding of the nature and advantages of embodiments of the present invention may be gained with reference to the following detailed description and the accompanying drawings.

DETAILED DESCRIPTION

Figure 1A:
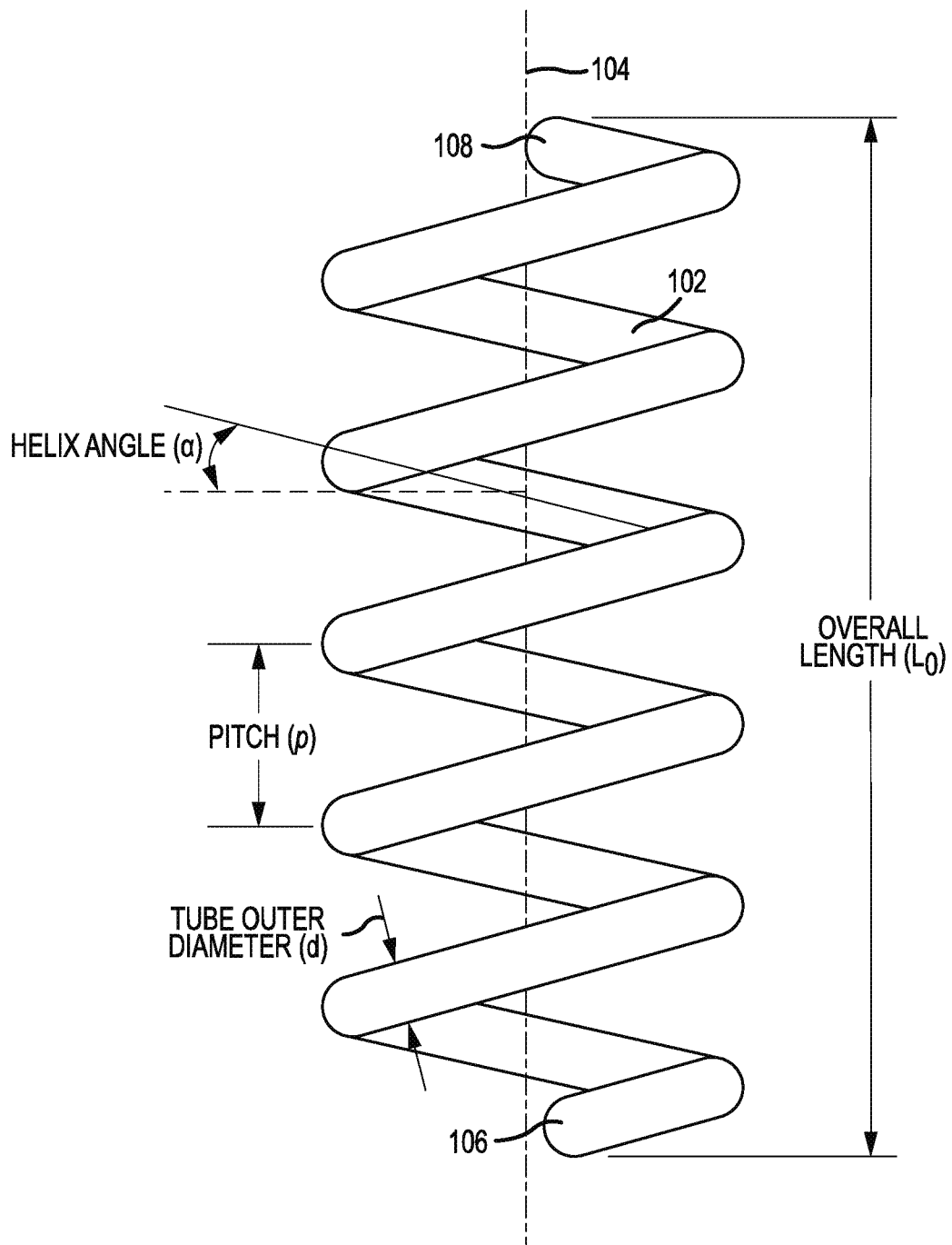
FIG. 1A and FIG. 1B show a helical mixer according to embodiments of the present technology.

Conventional emulsification methods may not result in a homogeneous emulsion. Conventional methods may result in convection currents that may create local eddies that disrupt flow and uniformity. In addition, conventional methods may include emulsifying mixers that occupy a large volume or footprint for the amount of emulsion produced. This large volume or footprint increases demand for manufacturing space and therefore increases the price of the process and final product.

Embodiments of the present technology may provide for a homogenous emulsion more efficiently than conventional methods. An aqueous phase and an oil phase may be flowed through a coiled tube to form an emulsion. Flow through a coiled tube may result in the formation of a secondary flow due to centrifugal forces. This secondary flow may create two symmetrical vortices perpendicular to the axial flow through the tube, stabilizing the fluid and preventing local eddies and random turbulence, which may allow mixing in a predictable manner. In order to further reduce turbulent flow and unpredictable mixing, the coiled tube may be packed with beads to reduce the available flow path and therefore reduce the Reynolds number. The beads may also serve to break up the fluids and aid in mixing.

In the bulk fluid, chaotic convection currents may develop, which may create non-uniformities in the emulsion. Convection currents may result within a mixture of a heavier component and a lighter component. The heavier component may move in the direction of gravity relative to the lighter component, while the lighter component may move against the direction of gravity relative to the heavier component, resulting in convection. Emulsions may include immiscible fluids of varying densities, which may result in temperature-independent convection. For example, emulsions may have a heavier oil phase and a lighter aqueous phase. To avoid this phenomenon, the mixture of the oil phase and the aqueous phase are flowed against the direction of gravity. As a result, because of the direction of flow, both the oil phase and the water phase may move in the same direction, reducing gravitational effects and therefore negating chaotic convection currents. In addition, when the flow through a mixer is in the same direction as gravity, the heavier component may move faster in the direction of gravity relative to the lighter component and therefore flow uncontrolled at a faster volumetric flow rate than the lighter component, again leading to non-uniformities in the emulsion or concentration gradients through the mixer. To avoid this and have better control of flow rates and a more controlled process, the mixture of the oil phase and the aqueous phase may be flowed against the direction of gravity. Furthermore, if the emulsion experiences a pressure drop a small amount of the organic solvent in the oil phase can possibly flash or can possibly be converted to a gaseous form. If this occurs, the gas bubbles may travel in the direction against gravity. The flow path of the emulsion may be in the same direction as any bubbles to avoid inadvertent turbulence generated by the emulsion and gas going in two different directions.

A coiled tube may also reduce the volume and footprint needed for emulsification. The vertical orientation of the coiled tube may reduce the footprint over a conventional mixer that may not be vertical. In addition, several coiled tubes can be nested together without increasing the footprint. Two coiled tubes nested together may resemble the structure of a double helix seen with DNA. Three coiled tubes nested together may resemble the structure of a triple helix similar to a collagen helix.

A mixed emulsion may be formed by forming one emulsion with an oil phase and an aqueous phase through a tube, another emulsion with an oil phase and an aqueous phase through another tube, and combining both emulsions. An advantage of using a mixed emulsion may be physically separating compounds that may interact with each other. The compounds that are physically separated may be two different physiologically active substances. Another advantage of using a mixed emulsion may be controlling the way the physiologically active substance is released. In this instance, one emulsion may include a different biodegradable polymer than the other. The two emulsions may differ in the concentration of the physiologically active substance.

Figure 7:
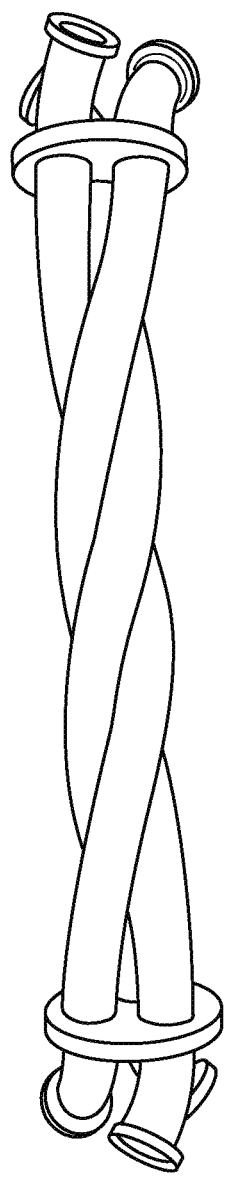
FIG. 7 shows a triple helical mixer according to embodiments of the present technology.

A mixed emulsion may also be formed by mixing emulsions produced by the same oil phase and oil phase flowing through several different tubes. By nesting multiple tubes together, such as the triple helical assembly, mixed emulsions may be used to scale up production, without increasing the laboratory bench space or manufacturing space. Examples of a triple helical assembly are shown in FIG. 3A and FIG. 7 and described below.

I. PHYSIOLOGICALLY ACTIVE SUBSTANCES

Physiologically active substance means a natural, synthetic, or genetically engineered chemical or biological compound that modulates physiological processes in order to afford diagnosis of, prophylaxis against, or treatment of an undesired existing condition in a living being. Physiologically active substances include drugs such as antianginas, antiarrhythmics, antiasthmatic agents, antibiotics, antidiabetics, antifungals, antihistamines, antihypertensives, antiparasitics, antineoplastics, antitumor drugs, antivirals, cardiac glycosides, herbicides, hormones, immunomodulators, monoclonal antibodies, neurotransmitters, nucleic acids, proteins, radio contrast agents, radionuclides, sedatives, analgesics, steroids, tranquilizers, vaccines, vasopressors, anesthetics, peptides, and the like. The physiologically active substance may include a small molecule. The small molecule may include budesonide or albuterol sulfate.

Prodrugs, which undergo conversion to the indicated physiologically active substances upon local interactions with the intracellular medium, cells, or tissues, can also be employed in embodiments. Any acceptable salt of a particular physiologically active substance, which is capable of forming such a salt, is also envisioned as useful in the present invention, including halide salts, phosphate salts, acetate salts, and other salts.

The physiologically active substances may be used alone or in combination. The amount of the substance in the pharmaceutical composition may be sufficient to enable the diagnosis of, prophylaxis against, or the treatment of an undesired existing condition in a living being. Generally, the dosage will vary with the age, condition, sex, and extent of the undesired condition in the patient, and can be determined by one skilled in the art. The dosage range appropriate for human use includes a range of 0.1 to 6,000 mg of the physiologically active substance per square meter of body surface area.

The pharmaceutical compositions of the invention can be administered parenterally by injection or by implantation. The compositions can be administered intravenously, intraperitoneally, intramuscularly, subcutaneously, intracavity, or transdermally. Other methods of administration will be known to those skilled in the art. For some applications, such as subcutaneous administration, the dose required may be quite small, but for other applications, such as intraperitoneal administration, the required dose may be very large. While doses outside the foregoing dosage range may be given, this range encompasses the breadth of use for practically all physiologically active substances. The pharmaceutical compositions of the invention can also be administered enterally.

Of particular interest are physiologically active substance that are proteins or peptides. The microparticles may include a protein or peptide compound. Proteins or peptides include insulin, human growth hormone, glucagon-like peptide-1, parathyroid hormone, a fragment of parathyroid hormone, enfuvirtide, or octreotide.

Insulin is normally produced by the pancreas. Insulin regulates the metabolism of glucose in the blood. A high level of glucose or other high blood sugar may be an indication of a disorder in the production of insulin and may be an indication of diabetes. Insulin is often administered by injection as a treatment for diabetes.

Another protein that may be used as a physiologically active substance is glucagon-like peptide-1 (GLP-1). GLP-1, a 31 amino acid peptide, is an incretin, a hormone that can decrease blood glucose levels. GLP-1 may affect blood glucose by stimulating insulin release and inhibiting glucagon release. GLP-1 also may slow the rate of absorption of nutrients into the bloodstream by reducing gastric emptying and may directly reduce food intake. The ability of GLP-1 to affect glucose levels has made GLP-1 a potential treatment for type 2 diabetes and other afflictions. In its unaltered state, GLP-1 has an in vivo half-life of less than two minutes as a result of proteolysis.

Proteins or peptides include human growth hormone. Human growth hormone (hGH), a 191 amino acid peptide, is a hormone that increases cell growth and regeneration. hGH may be used to treat growth disorders and deficiencies. For instance, hGH may be used to treat short stature in children or growth hormone deficiencies in adults. Conventional methods of administering hGH include daily subcutaneous injection.

Similar to hGH and GLP-1, enfuvirtide (Fuzeon®) is a physiologically active substance that may face challenges when administered to patients. Enfuvirtide may help treat HIV and AIDS. However, enfuvirtide may have to be injected subcutaneously twice a day. Injections may result in skin sensitivity reaction side effects, which may discourage patients from continuing use of enfuvirtide. A enfuvirtide treatment with less frequent administrations or extended duration may be needed to increase patient compliance, lower cost, and enhance the quality of life for patients with HIV and AIDS.

Another physiologically active substance is parathyroid hormone (PTH) or a fragment of PTH. PTH is an anabolic (bone forming) agent. PTH may be secreted by the parathyroid glands as a polypeptide containing 84 amino acids with a molecular weight of 9,425 Da. The first 34 amino acids may be the biologically active moiety of mineral homeostasis. A synthetic, truncated version of PTH is marketed by Eli Lilly and Company as Forteo® Teriparatide. PTH or a fragment of PTH may be used to treat osteoporosis and hypoparathyroidism. Teriparatide may often be used after other treatments as a result of its high cost and required daily injections. As with other physiologically active substances, a PTH treatment with less frequent administrations or extended duration may be desired.

Additional information on the proteins and conjugates of the proteins can be found in U.S. patent application Ser. No. 10/553,570, filed Apr. 8, 2004 (issued as U.S. Pat. No. 9,040,664 on May 26, 2015). Information regarding the concentration release profiles of proteins and conjugates can be found in U.S. patent application Ser. No. 14/954,701, filed Nov. 30, 2015. The contents of patent applications, publications, and all other references in this disclosure are incorporated herein by reference for all purposes.

II. SYSTEM

Embodiments of the present technology may include a system for forming an emulsion. The system may include a coiled tube or a helix. The coiled tube or helix may include chemically resistant materials such as stainless steel, ceramic, glass, various plastics (e.g., polytetrafluoroethylene [PTFE]), or other materials with a chemically resistant lining. As shown in FIG. 1A, coiled tube 102 may be coiled around a longitudinal axis 104. Longitudinal axis 104 may be vertical or substantially vertical. For example, the longitudinal axis may be within 0 degrees, 5 degrees, 10 degrees, 30 degrees, or 45 degrees off of vertical. Vertical may be in the direction of gravity. Coiled tube 102 may have a first end 106 and a second end 108. Second end 108 may be located at a position higher than the position of first end 106. Higher may mean away from the Earth.

Coiled tube 102 may be characterized by a helix. Coiled tube 102 may be characterized by a helix angle ranging from 2 to 85 degrees. A helix angle of 0 degrees may be horizontal, and a helix angle of 90 degrees may be vertical. Coiled tube 102 may be characterized by a pitch, p, which describes the linear distance between a point on a turn of the coil and the corresponding point on an adjacent turn of the coil. A turn of the coil may be defined as a full revolution around the longitudinal axis. Coiled tube 102 may have an overall length, $L_o$, along longitudinal axis 104. Coiled tube 102 may be a tube with an inner diameter of ⅛ inch to 10 inches.

Figure 5:
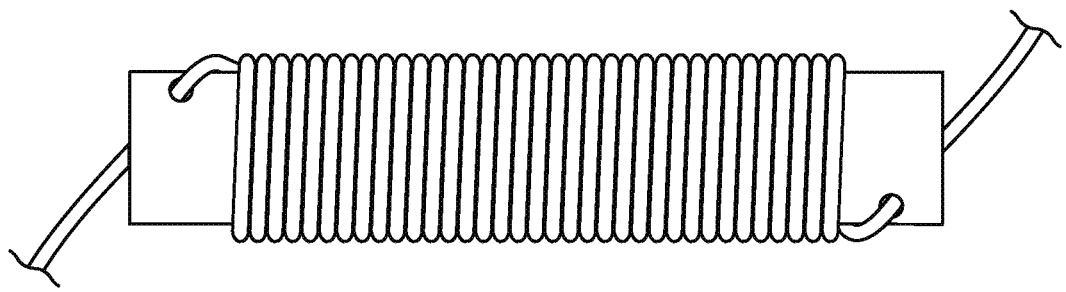
FIG. 5 shows a coiled tube mixer according to embodiments of the present technology.

The terms coil and helix may be distinguished based on the pitch, p, and helix angle, α. A helix is a type of coil. A coil can have little gap or no gaps between the coil. As a result, for a coil, the pitch can be zero or slightly greater than zero. A coil, however, is not limited to small pitches. For a helix, the pitch is greater than zero and is not zero. The helix angle, α, can be a small number for a coil because there may be no gaps between within the coil. For a helix, the angle is greater than zero and less than 90. An angle of 90 represents a linear tube that is neither a coil nor a helix. The coil or the helix may be right handed or left handed. FIG. 5 shows a coil, and FIG. 7 shows a helix. Coiled tubes described herein may include both helical tubes and non-helical, coiled tubes unless the context dictates otherwise. Embodiments may also exclude helical tubes or non-helical, coiled tubes.

Figure 1B:
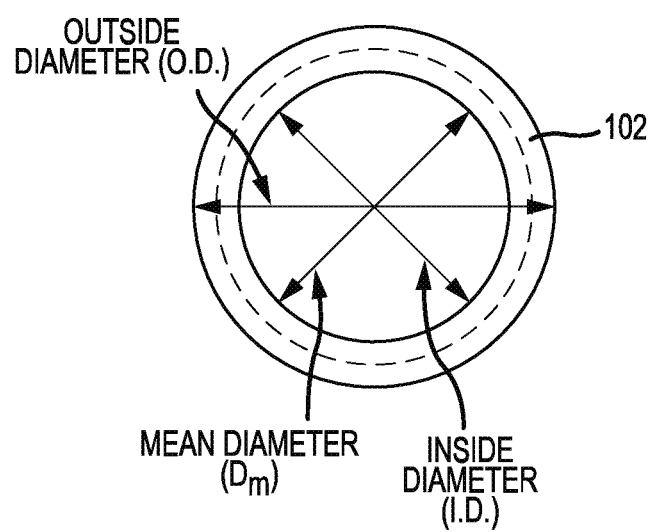

FIG. 1B shows an axial view of coiled tube 102. Coiled tube 102, when viewed axially, may appear to be a circle or an ellipse. The circle may be characterized by an outside diameter (O.D.), the distance from one outside edge of the circle to the farthest outside edge of the circle in a direction perpendicular to the longitudinal axis. The circle may be characterized by an inside diameter (I.D.), the distance from an inside edge of the circle to the farthest inner edge of the circle in a direction perpendicular to the longitudinal axis. The difference between the inside diameter and the outside diameter may be the outer diameter, d, of the tube. The circle may have a mean diameter that is the mean average of the inside and outside diameters. If a coiled tube viewed axially is an ellipse, then the ellipse may be characterized by a major axis and a minor axis. The helix angle, $\alpha$, may be related to the pitch, p, and the mean diameter, $D_m$, by the following equation:

$$\alpha = \tan^{-1}\left(\frac{p}{\pi D_m}\right).$$

The coiled tube may have a number of turns around the longitudinal axis ranging between 0.3 and 100, including from 0.3 to 1, from 1 to 10, from 10 to 20, from 20 to 30, from 30 to 50, from 50 to 75, or from 75 to 100. The coiled tube, if straightened out, may have an unwound length sufficient to create an average particle residence time of 0.5 seconds to 20 minutes.

A plurality of beads may be disposed within the coiled tube. The plurality of beads may be characterized by a median diameter of 2 mm, 1 mm, or 0.327 mm or any median diameter from 1 µm and 4 mm. A segregated combination of bead median diameters may also be used. The beads may include glass, borosilicate, ceramics, various plastics, or polymer materials. Preferably, the beads may include materials that are chemically resistant to interactions with the fluids flowing through the tube.

The tube may be filled with beads of different median diameters. For example, the bottom of the tube may be filled with a first plurality of beads of a certain median diameter, and the remainder of the tube may be filled with beads of monotonically decreasing or monotonically increasing median diameter. In other words, the tube may include a gradient of different median diameters. For example, a first plurality of beads having a median diameter of 1 mm may be used in combination with a second plurality of beads having a median diameter of 2 mm. The number of different pluralities of beads that differ in the median diameter may range from 2 and 10. Each median diameter for the different pluralities of beads may be statistically different from the others.

Figure 2:
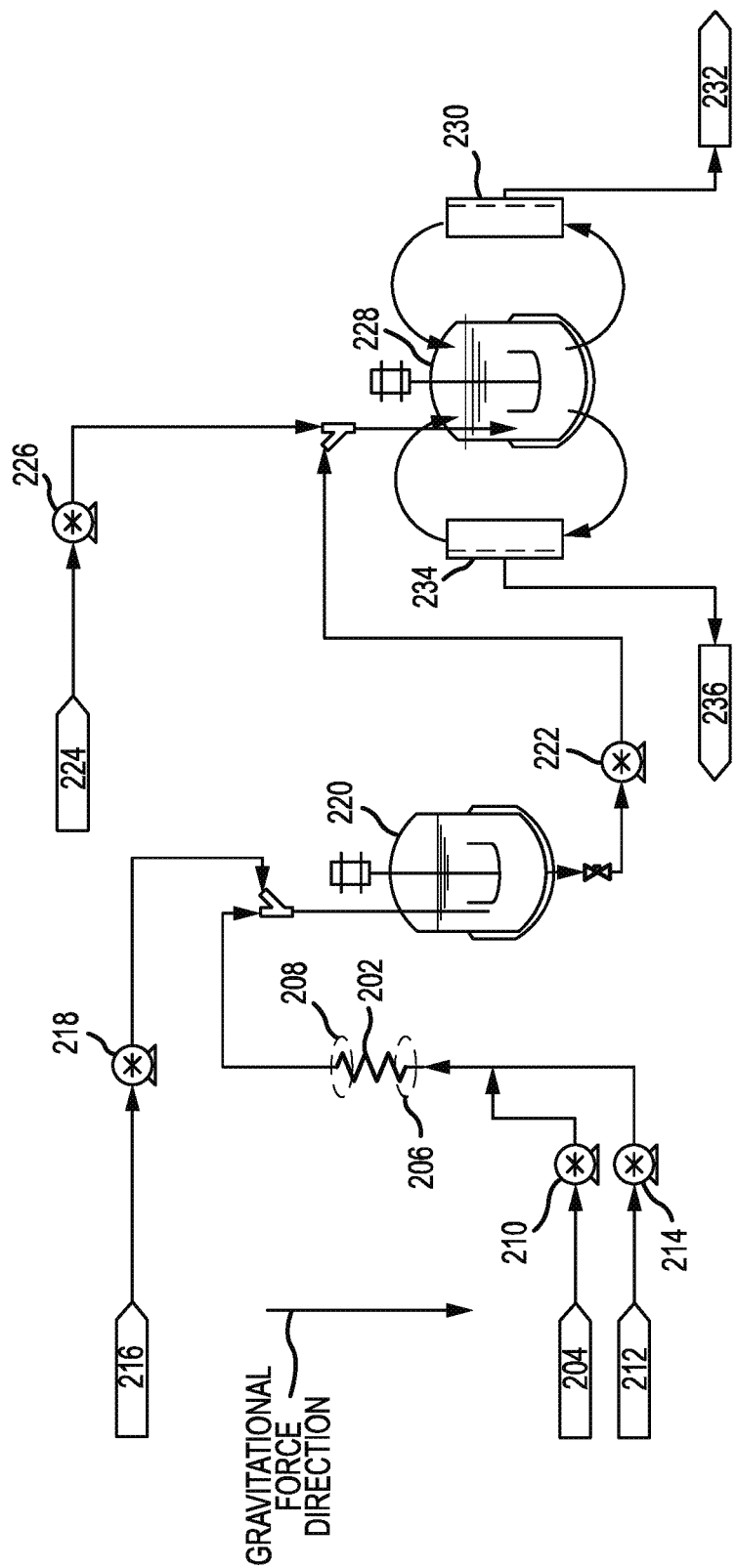
FIG. 2 shows a system for forming an emulsion and microparticles according to embodiments of the present technology.

FIG. 2 shows a system 200 for forming an emulsion and microparticles. System 200 may include a coiled tube 202. Coiled tube 202 may be any tube described herein. System 200 may further include a first inlet 204 fluidly connected to coiled tube 202. First inlet 204 may be configured to deliver a first fluid to first end 206 before second end 208. Coiled tube 202 may have its longitudinal axis aligned with the direction of gravity, as described herein. Hence, second end 208 may be above first end 206. The first fluid may be driven by a pump 210. The first fluid may be any oil stream or any aqueous stream described herein. In some embodiments, a screen may be located at either or both of first end 206 and second end 208.

In addition, system 200 may include a second inlet 212 fluidly connected to coiled tube 202. Second inlet 212 may be configured to deliver a second fluid to first end 206 before second end 208. The second fluid may be driven by pump 214. The second fluid may be any oil stream or any aqueous stream described herein. The second fluid may be a different stream than the first fluid. The first fluid and second fluid may both enter coiled tube 202.

A pump, such as pump 210 or pump 214, may be fluidly connected to the coiled tube. The pump may be configured to drive a flow of fluid from first end 206 to second end 208. The pump flowrates may be set to correspond with a Reynolds number from significantly less than 1 to 10,000, including from 0.1 to 0.5, from 0.5 to 1, 1 to 100, from 100 to 500, from 500 to 1,000, from 1,000 to 2,000, from 2,000 to 5,000, or from 5,000 to 10,000. The flow may also be driven without using pumps. For example, flow may be driven by applying pressure. The pressure may be a positive pressure, which is applied by forcing compressed air or a compressed gas to move a fluid from one location to another. The pressure may be a negative pressure, which is applied by using a vacuum to move a fluid from one location to another. System 200 may include a device for applying pressure to the fluid.

System 200 may include a third inlet 216 fluidly connected to coiled tube 202. Third inlet 216 may be in closer fluid communication with second end 208 than first end 206. A fluid entering through the third inlet may not enter coiled tube 202. Instead, the fluid entering through third inlet 216 may mix with the output of coiled tube 202. For example, third inlet 216 may deliver dilution water to mix with the emulsion formed after mixing an oil stream and an aqueous stream in the coiled tube. The fluid from third inlet 216 may be delivered using pump 218. The emulsion may form microparticles after being diluted with water or other diluents.

Third inlet 216 may lead to unit operations for concentrating microparticles and filtering microparticles. After being diluted, the microparticles may enter a first stirred tank reactor 220.

The outlet of first stirred tank reactor 220 may be pumped by pump 222. System 200 may include a fourth inlet 224. Fourth inlet 224 may be in closer fluid communication with second end 208 than first end 206. A fluid entering through the fourth inlet may not enter coiled tube 202. Instead, the fluid entering through fourth inlet 224 may mix with the output of first stirred tank reactor 220. For example, fourth inlet 224 may deliver dilution water to mix with the output of first stirred tank reactor 220. The fluid from fourth inlet 224 may be delivered using pump 226. The emulsion may form microparticles after being diluted with water or other diluents.

The mixture of fluid from fourth inlet 224 and the output of first stirred tank reactor 220 may flow to second stirred tank reactor 228. Second stirred tank reactor 228 may be fluidly connected to a plurality of screens. Screen 230 may remove wastewater and fines. Screen 230 may have a size ranging from 5 µm to 40 µm, including about 25 µm. Fines and wastewater may pass through screen 230 and be sent to waste outlet 232.

Second stirred tank reactor 228 may be fluidly connected to screen 234. Screen 234 may have a size of 50 µm to 250 µm, including about 100 µm. Process fluid including spheres of a desired size flow through screen 234 and proceed to a drying step through outlet 236. Larger size particles are rejected by screen 234. Coiled tube 202 may be fluidly connected to screens 230 and 234 through second stirred tank reactor 228. The plurality of screens may be in closer fluid communication with second end 208 than first end 206. Screens 230 and 234 may be simultaneously processing fluid from second stirred tank reactor 228. Flow may recirculate between screen 230, screen 234, and second stirred tank reactor 228.

In some embodiments, coiled tube 202 may be a first coiled tube out of a plurality of coiled tubes. The first coiled tube may be coiled around a longitudinal axis. The first coiled tube may be characterized by a first width in a direction perpendicular to the longitudinal axis. For example, the first width may be the outside diameter, inner diameter, or mean diameter in FIG. 1B. The system may include a second coiled tube. The second coiled tube may include a second plurality of beads disposed therein. The second coiled tube may be coaxial with the longitudinal axis. The second coiled tube may be characterized by a second width in a direction perpendicular to the longitudinal axis. For example, the second width may be the corresponding diameter as for the first coiled tube. The first coiled tube and the second coiled tube are arranged such that a pair of the first coiled tube and the second coiled tube may be characterized by a third width perpendicular to the longitudinal axis. The third width may equal to the first width and to the second width. The third width may be the corresponding diameter for the two coiled tubes together. In some embodiments, the system may include a third coiled tube nested with the two coiled tubes.

Figure 3B:
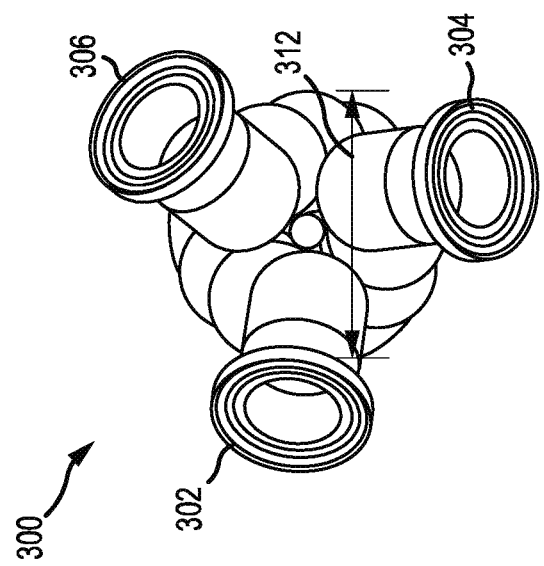
FIG. 3A and FIG. 3B show a set of three helical tubes according to embodiments of the present technology.
Figure 3A:
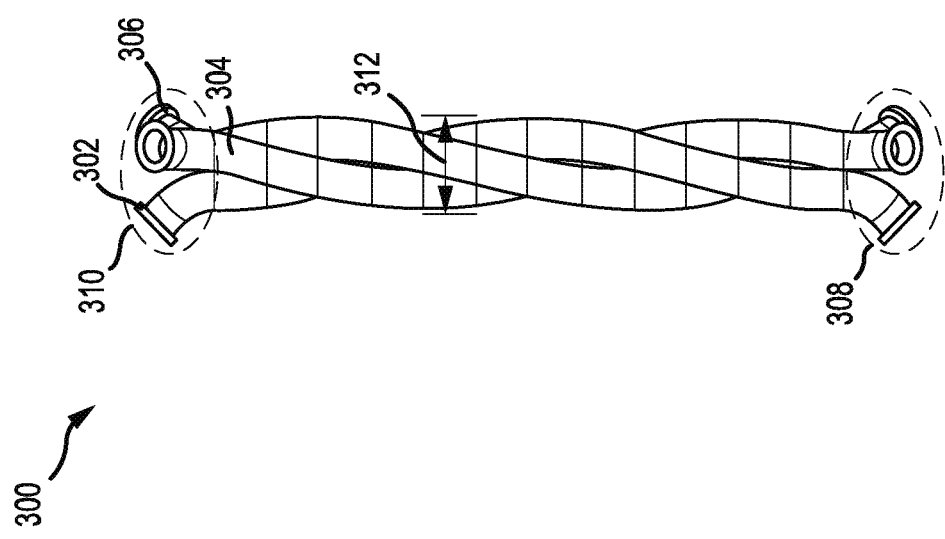

FIG. 3A and FIG. 3B show a set 300 of three coiled tubes (coiled tube 302, coiled tube 304, coiled tube 306) nested together. Although three coiled tubes are shown, any other plurality of coiled tubes may be nested together. Each coiled tube may be any tube described herein. For each tube of the plurality of coiled tubes, the coiled tube may include a first end in region 308 and a second end in region 310. The second end may be disposed at a position higher than the position of the first end. Set 300 may be substituted for coiled tube 202 in FIG. 2. For each coiled tube, a first inlet may be fluidly connected to the coiled tube, where the first inlet is configured to deliver a first fluid to the first end before the second end. Also for each coiled tube, a second inlet may be fluidly connected to the coiled tube, where the second inlet is configured to deliver a second fluid to the first end before the second end. A plurality of beads may be disposed within the coiled tubes. The first inlet, the second inlet, and the plurality of beads may be any described herein.

Each coiled tube may be coiled around a longitudinal axis. Each coiled tube may be characterized by a first width in a direction perpendicular to the longitudinal axis. The first width may be the outer diameter, inner diameter, or mean diameter. The plurality of coiled tubes may be coaxial with the longitudinal axis. In addition, the plurality of coiled tubes may be characterized by a second width in a direction perpendicular to the longitudinal axis. The second width may be the outer diameter, inner diameter, or mean diameter for the plurality of tubes. The first width may equal the second width. For example, the second width may be outer diameter 312.

Each coiled tube of the plurality of coiled tubes may be characterized by a first height in the direction of the longitudinal axis. The plurality of coiled tubes may be characterized by a second height in the direction of the longitudinal axis. The first height may be equal to the second height. Each coiled tube may have the same helix angle, pitch, length, tube outer diameter, and/or tube inner diameter as the other coiled tubes. In other words, each coiled tube may be substantially identical to the other coiled tubes.

III. METHODS

Figure 4:
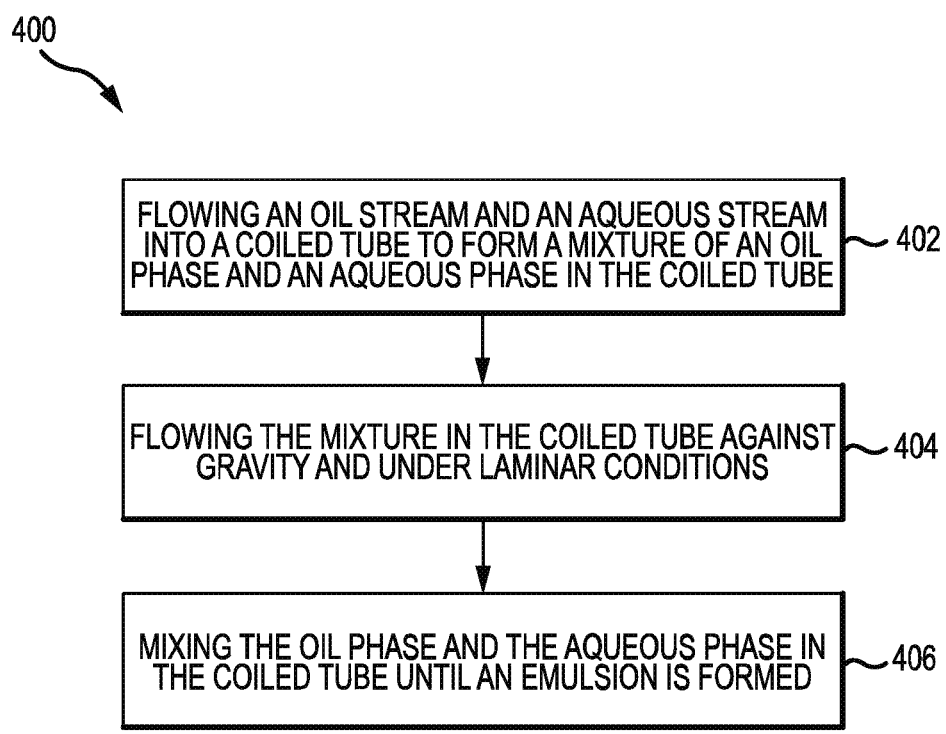
FIG. 4 shows a method of forming an emulsion according to embodiments of the present technology.

FIG. 4 shows a method 400 of forming an emulsion. Method 400 may include flowing an oil stream and an aqueous stream into a coiled tube to form a mixture of an oil phase and an aqueous phase in the coiled tube (block 402). The coiled tube may be any coiled tube described herein. Method 400 may be performed using system 200 and/or set 300.

The oil stream may include a biodegradable polymer. The biodegradable polymer may include a polylactide, a polyglycolide, a poly(d,l-lactide-co-glycolide), a polycaprolactone, a polyorthoester, a copolymer of a polyester and a polyether, or a copolymer of polylactide and polyethylene glycol. The biodegradable polymer may exclude any of these polymers or groups of these polymers. The molecular weight of the biodegradable polymer may be adjusted to produce a desired pharmacokinetic profile.

Poly(d,l-lactide-co-glycolide) (PLGA) may have a molecular weight from 5,000 Da to 7,000 Da, 7,000 Da to 17,000 Da, 17,000 Da to 20,000 Da, 20,000 Da to 24,000 Da, 24,000 Da to 38,000 Da, 38,000 Da to 40,000 Da, or 40,000 Da to 50,000 Da, in examples. PLGA may have a molar ratio of lactide to glycolide of 50:50 or 75:25. In some examples, PLGA may have a ratio of lactide to glycolide ranging from 40:60 to 50:50, from 50:50 to 60:40, from 60:40 to 70:30, from 70:30 to 75:25, or from 75:25 to 90:10. The ratio of lactide to glycolide may be less than or equal to 50:50, less than or equal to 60:40, or less than or equal to 75:25, where less than refers to a smaller proportion of lactide compared to glycolide. The hydrophobic anion of the organic acid may improve the release characteristics of some PLGAs but not others.

Possible PLGAs may include PLGA 502, PLGA 503, PLGA 752, and PLGA 753. PLGA 502 may be a polymer with a lactide to glycolide ratio of 50:50, an inherent viscosity from 0.16 to 0.24 dL/g, and a molecular weight from 7,000 to 17,000 Da. PLGA 503 may be a polymer with a lactide to glycolide ratio of 50:50, an inherent viscosity from 0.32 to 0.44 dL/g, and a molecular weight from 24,000 to 38,000 Da. PLGA 752 may be a polymer with a lactide to glycolide ratio of 75:25, an inherent viscosity from 0.14 to 0.22 dL/g, and a molecular weight from 4,000 to 15,000 Da. PLGA 753 may be a polymer with a lactide to glycolide ratio of 75:25, an inherent viscosity from 0.32 to 0.44 dL/g, and a molecular weight from 24,000 to 38,000 Da. The PLGA polymer may also be acid end-capped or ester end-capped.

The oil stream may include a physiologically active substance The physiologically active substance may be a protein, peptide compound, or a small molecule. The protein or peptide compound may include a protein-PEG conjugate or a peptide-PEG conjugate. The protein or peptide compound may be any protein or peptide compound described herein. Physiologically active substances may include those that dissolve in the organic solvent in the presence of the biodegradable polymer.

The oil stream may include an organic solvent. The organic solvent may include methylene chloride, benzyl benzoate, dichloromethane, chloroform, ethyl ether, ethyl acetate, acetic acid isopropyl ester (isopropyl acetate), acetic acid sec-butyl ester, acetophenone, n-amyl acetate, aniline, benzaldehyde, benzene, benzophenone, benzyl alcohol, benzyl amine, bromobenzene, bromoform, n-butyl acetate, butyric acid methyl ester, caproic acid, carbon disulfide, carbon tetrachloride, o-chloroaniline, chlorobenzene, 1-chlorobutane, chloromethane, m-chlorophenol, m-cresol, o-cresol, cyanoethane, cyanopropane, cyclohexanol, cyclohexanone, 1,2-dibromoethane, dibromomethane, dibutyl amine, m-dichlorobenzene, o-dichlorobenzene, 1,1-dichloroethane, 1,2-dichloroethane, dichlorofluoromethane, diethyl carbonate, diethyl malonate, diethyl sulfide, diethylene glycol dibutyl ether, diisobutyl ketone, diisopropyl sulfide, dimethyl phthalate, dimethyl sulfate, dimethyl sulfide, N,N-dimethylaniline, enanthic acid, ethyl acetoacetate, ethyl benzoate, ethyl propionate, ethylbenzene, ethylene glycol monobutyl ether acetate, exxate 600, exxate 800, exxate 900, fluorobenzene, furan, hexamethylphosphoramide, 1-hexanol, n-hexyl acetate, isoamyl alcohol (3-methyl-1-butanol), isobutyl acetate, methoxybenzene, methyl amyl ketone, methyl benzoate, methyl formate, methyl isoamyl ketone, methyl isobutenyl ketone, methyl isobutyl ketone, methyl n-butyl ketone, methyl propyl ketone, 4-methyl-2-pentanol, N-methylaniline, nitrobenzene, nitroethane, 1-nitropropane, 2-nitropropane, 1-octanol, 2-octanol, 1-pentanol, 3-pentanone, 2-phenylethanol, n-propyl acetate, quinoline, styrene, 1,1,2,2-tetrachloroethane, 1,1,2,2-tetrachloroethylene, toluene, 1,1,1-trichloroethane, 1,1,2-trichloroethane, 1,1,2-trichloroethylene, trifluoromethane, valeric acid, m-xylene, o-xylene, p-xylene, 2,4-xylenol, or mixtures thereof. The organic solvent may exclude any solvent or any groups of solvents.

Methods may include a mixture of solvents. The mixture of solvents may include a solvent that is miscible in water, but the mixture of solvents may be immiscible in water. For examples, a water-miscible solvent such as dimethyl sulfoxide (DMSO), methanol, dimethylformamide (DMF), acetonitrile, tetrahydrofuran, or mixtures thereof may be added to the water immiscible solvent.

The oil stream may include a hydrophobic anion. The hydrophobic anion may include anions associated with the hydrophobic organic acids. For example, the hydrophobic anion may include a pamoate anion, a docusate anion, or a furoate anion. In these or other examples, the hydrophobic anion may be a fatty acid anion, a phospholipid anion, a polystyrene sulfonate anion, or mixtures thereof. The phospholipid of the phospholipid anion may include phosphatidylcholine, phosphatidylglycerol, phosphatidylserine, phosphatidylinositol, phosphatidylethanolamine, phosphocholine, or mixtures thereof. The hydrophobic anion may also exclude any anion described or any group of anions described. The hydrophobic anion may attach to a specific side chain on the protein or it may attach to multiple side chains on the protein. The hydrophobic anion may have a log P greater than 1. The log P is the water-octanol partition coefficient and may be defined as the logarithm of the concentration of the protein salt in octanol to the concentration of the protein salt in water. A log P greater than 1 may result in a concentration in octanol that is 10 times greater than that in water. The water-octanol partition coefficient may be useful in comparing different molecules for their ability to partition into a hydrophobic phase, when the molecules themselves may be amphipathic. Methods may also include adding cationic detergents, such as dodecylamine hydrochloride or cetyltrimethylammonium bromide (CTAB), which may counter the charge of negatively charged peptides and may increase the hydrophobicity.

The aqueous stream may include water and an emulsion stabilizer such as polyvinyl alcohol (PVA), may contain some organic solvent, buffers, salts, and/or hydrophobic ions. The aqueous stream may contain a physiologically active substance. Physiologically active substances may include water soluble proteins, peptides, or small molecules. The physiologically active substance may also include PEG-conjugates or any physiologically active substance described herein.

At block 404, method 400 may also include flowing the mixture in the coiled tube against gravity and under laminar conditions. The flow of the mixture in the coiled tube may have a Reynolds number ranging from significantly less than 1 to 10,000. A plurality of beads may be disposed within the coiled tube. The beads may be any beads described herein. The flow in the coiled tube may reduce, minimize, or eliminate chaotic convection mixing.

At block 406, method 400 may further include mixing the oil phase and the aqueous phase in the coiled tube until the emulsion is formed. The emulsion formed may be homogenous. Homogeneity of the emulsion may be determined by the particle size distribution. Particle size distribution profiles may be predominantly unimodal. Particles that are not part of the unimodal particle size distribution profile may be no more than 25 vol % of the particles. For example, microparticles with diameters smaller than the lower end of the unimodal particle size distribution may total less than 25 vol %, less than 10 vol %, less than 5 vol. %, less than 2 vol. %, or less than 1 vol. % of the total.

Method 400 may further include diluting the emulsion with water. Method 400 may also include forming microparticles from the emulsion. Forming microparticles may include removing water and solvent from the emulsion. The microparticles may include a protein or peptide compound, a PEG conjugate or a small molecule. The microparticles may have a median diameter in a range from 1 to 99 µm. The microparticles may be microspheres. The diameter of the microparticles may be chosen based on the route of administration. When the microparticles are intended to be implanted in the body as a solid, the diameter may be in the range of less than 1 µm and several centimeters. The upper range may be an inch. When the microparticles are intended to be injected as a suspension under the skin or into the muscle, the microparticles may have a smaller diameter and may be based on the dimensions of a needle. The inner diameter of needles used to inject suspensions under the skin or into the muscle may be in the range of several hundreds to several thousands of micrometers. For example, a needle of gauge 7 has an inner diameter of approximately 3.81 mm. A needle of gauge 34 has an inner diameter of approximately 0.0826 mm. Microparticles injected using needles in the gauge range of 7 and 34 may have diameters in the range of less than 1 µm and 3,000 µm. Diameters of microparticles for narrower gauge needles may range from 10 µm to 90 µm, 20 µm to 70 or 25 µm to 63 µm.

IV. EXAMPLES

For the examples, the Reynolds number was calculated in two different ways. For the helical emulsifiers without packing, the Reynolds number, Re, may be related to the fluid velocity, V, the diameter of the tube, $D_{tube}$, and the kinematic viscosity of the fluid, v, by the following equation:

$$Re = \frac{VD_{tube}}{v}.$$

For the packed helical emulsifiers, the Reynolds number may be related to the superficial fluid velocity, V, the average particle diameter of the packing, $D_p$, and the kinematic viscosity of the fluid, ν, by the following equation:

$$Re = \frac{VD_p}{v}.$$

The critical Reynolds number, the Reynolds number that corresponds with a maximum in the laminar flow regime, for straight tubes is 2100. However, for coiled tubes, when a fluid is forced to follow a curved path, centrifugal forces may create Dean vortices, or a secondary flow perpendicular to the axial, primary flow. This secondary flow may have a stabilizing effect. Flow through a coil, therefore, may suppress turbulent fluctuations and smoothes the emergence of turbulence, increasing the value of the critical Reynolds number, as compared to that of as straight pipe. The critical Reynolds number through a coiled tube, $Re_{cr}$, may be related to the diameter of the tube, $D_{tube}$, and the diameter of the coil, $D_c$, by the following equation:

$$Re_{cr} = 2100\left(1 + 12\sqrt{\frac{D_{tube}}{D_c}}\right).$$

This stabilizing effect allows for larger diameters of process equipment, or higher flow rates, and therefore higher throughput and shorter processing time while still allowing for gentle mixing of the emulsion.

In order to report a practical range of possible Reynolds numbers through the helical emulsifiers in these examples, two kinematic viscosities were used. An upper bound was determined by assuming the kinematic viscosity to be that of pure water at 20° C., 1.002 centistokes. The kinematic viscosity of the emulsion was also experimentally determined using a Cannon-Fenske viscometer. The experimental viscosity of the emulsion, 17.6 centistokes, was significantly greater than that of water yielding a lower bound on the calculated Reynolds number range for each example.

A. Examples 1-3

Examples 1-3 show the viability of the helical emulsifier for making an emulsion that can be used to make microspheres. The particle size can be tuned by adjusting the number of coils or the diameter of the helix. The particle size increases as the number of coils increases.

Example 1

A coiled tube mixer, shown in FIG. 5, for the preparation of polymer microspheres was created by wrapping ⅛ inch PTFE tubing (1/16" inner diameter) around a 1.1-inch diameter cylinder for a total of 35 complete coils. The resulting coil has a mean diameter of 1.2 inches and a helix angle of 2 degrees.

These dimensions increase the critical Reynolds number to a value of 7,851. A tee was connected at the inlet for the introduction of two unmixed liquid phases. A second tee was connected to the outlet of the helix for the introduction of an emulsion dilution phase.

An 8.8% w/w polymer-in-oil oil phase (Oil Phase) was prepared by dissolving 8.5 grams of 50:50 poly(lactic-co-glycolic acid) (PLGA) (Resomer Select 5050 DLG 2A, Lot number LP1487, Evonik Corp.) in 88 grams of dichloromethane (DCM) and allowed to stir overnight at room temperature (~19° C.). A second solution (Water Phase) was made by dissolving 2.67 grams of poly(vinyl alcohol) (PVA) in 267 milliliters of deionized water overnight. A dilution phase was prepared by tempering deionized water to a temperature of 19° C. The Oil Phase was pumped through the assembly at a rate of 61 ml/min while the Water Phase was concurrently pumped through the same assembly at a rate of 160 ml/min. The resulting Reynolds number through the apparatus was laminar, falling between 168 and 2,948, which is well below the critical Reynolds number of 7,851 for this mixer. Upon leaving the helical apparatus, the emulsion was diluted using deionized water pumped at a rate of 1,280 ml/min. The particle size distribution of the emulsion was then analyzed using laser diffraction (Beckman Coulter LS 13 320). The median particle size (d50) of the emulsion was found to be 65 microns with a d10 of 31 μm and a d90 of 130 The percentage of particles between 25 and 63 microns was 45% by volume.

Example 2

A helical mixer for the preparation of polymer microspheres was created by wrapping ⅛ inch PTFE tubing (1/16" inner diameter) around a 1.1-inch diameter cylinder for a total of 70 complete coils. The resulting helix has a mean diameter of 1.3 inches and a helix angle of 2 degrees. In the current example, these dimensions increase the critical Reynolds number to a value of 7,625. A tee was connected at the inlet for the introduction of two unmixed liquid phases. A second tee was connected to the outlet of the helix for the introduction of an emulsion dilution phase.

An 8.8% w/w polymer-in-oil oil phase (Oil Phase) was prepared by dissolving 8.5 grams of 50:50 poly(lactic-co-glycolic acid) (PLGA) (Resomer Select 5050 DLG 2A, Lot number LP1487, Evonik Corp.) in 88 grams of dichloromethane (DCM) and allowed to stir overnight at room temperature (~19° C.). A second solution (Water Phase) was made by dissolving 2.67 grams of poly(vinyl alcohol) (PVA) in 267 milliliters of deionized water overnight. A dilution phase was prepared by tempering deionized water to a temperature of 19° C. The Oil Phase was pumped through the assembly at a rate of 30 ml/min while the Water Phase was concurrently pumped through the same assembly at a rate of 160 ml/min. The resulting Reynolds number through the apparatus was laminar, falling between 144 and 2,535, which is well below the critical Reynolds number of 7,625 for this mixer. Upon leaving the helical apparatus, the emulsion was diluted using deionized water pumped at a rate of 1,280 ml/min. The particle size distribution of the emulsion was then analyzed using laser diffraction (Beckman Coulter LS 13 320). The median particle size (d50) of the emulsion was found to be 96 microns with a d10 of 51 μm and a d90 of 133 μm. The percentage of particles between 25 and 63 microns was 14% by volume.

Example 3

A helical mixer for the preparation of polymer microspheres was created by wrapping ⅛ inch PTFE tubing (1/16" inner diameter) around a 0.63-inch diameter cylinder for a total of 55 complete coils. The resulting helix has a mean diameter of 0.75 inches and a helix angle of 3 degrees. In the current example, these dimensions increase the critical Reynolds number to a value of 9,375. A tee was connected at the inlet for the introduction of two unmixed liquid phases. A second tee was connected to the outlet of the helix for the introduction of an emulsion dilution phase.

An 8.8% w/w polymer-in-oil oil phase (Oil Phase) was prepared by dissolving 8.5 grams of 50:50 poly(lactic-co-glycolic acid) (PLGA) (Resomer Select 5050 DLG 2A, Lot number LP1487, Evonik Corp.) in 88 grams of dichloromethane (DCM) and allowed to stir overnight at room temperature (~19° C.). A second solution (Water Phase) was made by dissolving 2.67 grams of poly(vinyl alcohol) (PVA) in 267 milliliters of deionized water overnight. A dilution phase was prepared by tempering deionized water to a temperature of 19° C. The Oil Phase was pumped through the assembly at a rate of 61 ml/min while the Water Phase was concurrently pumped through the same assembly at a rate of 160 ml/min. The resulting Reynolds number through the apparatus was laminar, falling between 168 and 2,948, which is well below the critical Reynolds number of 9,375 for this mixer. Upon leaving the helical apparatus, the emulsion was diluted using deionized water pumped at a rate of 1,230 ml/min. The particle size distribution of the emulsion was then analyzed using laser diffraction (Beckman Coulter LS 13 320). The median particle size (d50) of the emulsion was found to be 88 microns with a d10 of 40 μm and a d90 of 320 μm. The percentage of particles between 25 and 63 μm was 21% by volume.

Examples 1-3 Summary

TABLE 1

| | Helical Emulsifier | | | Process Parameters | Resulting Particle Size Distribution of |  |  |  |  |
|---|---|---|---|---|---|---|---|---|---|
| | | | | Total | Microspheres | | | | |
| | | | | Flow | | | | | Particles |
| Example | Number of Coils | Mean Diameter (in) | Tubing ID (in) | Through Emulsifier (ml/min) | Measured Reynolds Number | Median (μm) | d10 (μm) | d90 (μm) | between 25 um and 63 um (vol %) |
| 1 | 35 | 1.18 | 0.063 | 221 | 168 | 65 | 31 | 130 | 45 |
| 2 | 70 | 1.26 | 0.063 | 190 | 144 | 96 | 51 | 133 | 14 |
| 3 | 55 | 0.75 | 0.063 | 221 | 168 | 88 | 40 | 320 | 21 |

These examples show that the helical mixer can be used to make an emulsion that is appropriate for forming microspheres. The resulting particle size distribution is larger and more variable than desired for injection through large gauge (small diameter) needles. For injection through small diameter needles, a particle size range from 25 to about 63 μm is desired. The percent of material in the desired particle size range is less than 45% for these examples. These data also show that the particle size distribution can be adjusted by changing both the number of coils and the mean diameter of the coils.

B. Examples 4-6

Examples 4-6 show continued functionality of the helical mixer (without packing with beads) for making an emulsion that can be used to make microspheres. In these examples, the particle size is adjusted by using different flow rates. Faster flow rates result in smaller particle size.

A helical mixer for the preparation of polymer microspheres was created by wrapping ⅛ inch PTFE tubing (1/16" inner diameter) around a 0.62-inch diameter cylinder for a total of 22 complete coils. The resulting helix has a mean diameter of 0.75 inches and a helix angle of 3 degrees. For this apparatus, these dimensions increase the critical Reynolds number to a value of 9,375. A tee was connected at the inlet for the introduction of two unmixed liquid phases. A second tee was connected to the outlet of the helix for the introduction of an emulsion dilution phase. This assembly was used during the following three examples.

Example 4

An 8.8% w/w polymer-in-oil oil phase (Oil Phase) was prepared by dissolving 8.5 grams of 50:50 poly(lactic-co-glycolic acid) (PLGA) (Resomer Select 5050 DLG 2A, Lot number LP1487, Evonik Corp.) in 88 grams of dichloromethane (DCM) and allowed to stir overnight at room temperature (~19° C.). A second solution (Water Phase) was made by dissolving 2.67 grams of poly(vinyl alcohol) (PVA) in 267 milliliters of deionized water overnight. A dilution phase was prepared by tempering deionized water to a temperature of 19° C. The Oil Phase was pumped through the helical apparatus at a rate of 61 ml/min while the Water Phase was concurrently pumped through the helical apparatus at a rate of 160 ml/min. The resulting Reynolds number through the apparatus was laminar, falling between 168 and 2,948, which is well below the critical Reynolds number of 9,375 for this mixer. Upon leaving the helical apparatus the emulsion was diluted using deionized water pumped at a rate of 1230 ml/min. The particle size distribution of the emulsion was then analyzed using laser diffraction (Beckman Coulter LS 13 320). The volumetric median particle size of the emulsion was found to be 62 μm with a d10 of 25 μm and a d90 of 119 μm. The percentage of particles between 25 and 63 microns was 44% by volume.

Example 5

An 8.8% w/w polymer-in-oil oil phase (Oil Phase) was prepared by dissolving 8.5 grams of 50:50 poly(lactic-co-glycolic acid) (PLGA) (Resomer Select 5050 DLG 2A, Lot number LP1487, Evonik Corp.) in 88 grams of dichloromethane (DCM) and allowed to stir overnight at room temperature (~19° C.). A second solution (Water Phase) was made by dissolving 2.67 grams of poly(vinyl alcohol) (PVA) in 267 milliliters of deionized water overnight. A dilution phase was prepared by tempering deionized water to a temperature of 19° C. The Oil Phase was pumped through the helical apparatus at a rate of 61 ml/min while the Water Phase was concurrently pumped through the helical appa-ratus at a rate of 250 ml/min. The resulting Reynolds number through the apparatus was laminar, falling between 236 and 4,149, which is well below the critical Reynolds number of 9,375 for this mixer. Upon leaving the helical apparatus the emulsion was diluted using deionized water pumped at a rate of 1,230 ml/min. The particle size distribution of the emulsion was then analyzed using laser diffraction (Beckman Coulter LS 13 320). The volumetric median particle size of the emulsion was found to be 41 μm with a d10 of 13 μm and a d90 of 90 μm. The percentage of particles between 25 and 63 microns was 59% by volume.

Example 6

An 8.8% w/w polymer-in-oil oil phase (Oil Phase) was prepared by dissolving 8.5 grams of 50:50 poly(lactic-co-glycolic acid) (PLGA) (Resomer Select 5050 DLG 2A, Lot number LP1487, Evonik Corp.) in 88 grams of dichloromethane (DCM) and allowed to stir overnight at room temperature (~19 C). A second solution (Water Phase) was made by dissolving 2.67 grams of poly(vinyl alcohol) (PVA) in 267 milliliters of deionized water overnight. A dilution phase was prepared by tempering deionized water to a temperature of 19° C. The Oil Phase was pumped through the helical apparatus at a rate of 9 ml/min, while the Water Phase and the dilution water were concurrently pumped through the helical apparatus at a rate of 21 ml/min and 120 ml/min, respectively. The resulting Reynolds number through the apparatus was laminar, falling between 114 and 2,001, which is well below the critical Reynolds number of 9,375 for this mixer. The particle size distribution of the emulsion was then analyzed using laser diffraction (Beckman Coulter LS 13 320). The median particle size of the emulsion was found to be 164 microns with a d10 of 83 μm and a d90 of 221 μm. The percentage of particles between 25 and 63 microns was 3.5% by volume.

Examples 4-6 Summary

TABLE 2

| | Helical Emulsifier | | | Process Parameters | | Resulting Particle Size Distribution of Microspheres | | | |
|---|---|---|---|---|---|---|---|---|---|
| | | | | Total Flow | | | | | Particles |
| Example | Number of Coils | Mean Diameter (in) | Tubing ID (in) | Through Emulsifier (ml/min) | Measured Reynolds Number | Median (μm) | d10 (μm) | d90 (μm) | between 25 um and 63 um (vol %) |
| 4 | 22 | 0.75 | 0.063 | 221 | 168 | 62 | 25 | 119 | 44 |
| 5 | 22 | 0.75 | 0.063 | 311 | 236 | 41 | 13 | 90 | 59 |
| 6 | 22 | 0.75 | 0.063 | 150 | 114 | 164 | 83 | 221 | 3.5 |

These examples show that the helical mixer can be used to make an emulsion that is appropriate for forming microspheres. The flow rate through the emulsifier directly affects the particle size distribution, with faster flow resulting in smaller particles. The particle size is larger and more variable than desired for injection through large gauge (small diameter) needles. In these examples, the percent of material in the desired particle size range is less than or equal to 59% by volume.

C. Examples 7-17

Examples 7-17 show continued functionality of the helical mixer (without packing with beads) for making an emulsion that can be used to make microspheres. In these examples, the particle size is adjusted by using screens on the entrance and/or exit of the mixer to adjust the particle size distribution.

A helical mixer for the preparation of polymer microspheres was created by wrapping ⅛ inch PTFE tubing (1/16" inner diameter) around a 0.62-inch diameter cylinder for a total of 22 complete coils. The resulting helix has a mean diameter of 0.75 inches and a helix angle of 3 degrees. For this apparatus, these dimensions increase the critical Reynolds number to a value of 9,375. A tee was connected at the inlet for the introduction of two unmixed liquid phases. A second tee was connected to the outlet of the helix for the introduction of an emulsion dilution phase. This assembly was used during the following eleven examples.

Example 7

An 8.8% w/w polymer-in-oil oil phase (Oil Phase) was prepared by dissolving 8.5 grams of 50:50 poly(lactic-co-glycolic acid) (PLGA) (Resomer Select 5050 DLG 2A, Lot number LP1487, Evonik Corp.) in 88 grams of dichloromethane (DCM) and allowed to stir overnight at room temperature (~19° C.). A second solution (Water Phase) was made by dissolving 2.67 grams of poly(vinyl alcohol) (PVA) in 267 milliliters of deionized water overnight. A dilution phase was prepared by tempering deionized water to a temperature of 19° C. A screen was placed between the inlet tee and the helical apparatus with a mesh size of 120 by 500 (35 μm approximate retention). The Oil Phase was pumped through the assembly at a rate of 61 ml/min while the Water Phase was concurrently pumped through the same assembly at a rate of 190 ml/min. The resulting Reynolds number through the apparatus was laminar, falling between 191 and 3,349, which is well below the critical Reynolds number of 9,375 for this mixer. Upon leaving the helical apparatus, the emulsion was diluted using deionized water pumped at a rate of 1,200 ml/min. The particle size distribution of the emulsion was then analyzed using laser diffraction (Beckman Coulter LS 13 320). The median particle size (d50) of the emulsion was found to be 45 microns with a d10 of 20 μm and a d90 of 80 μm. The percentage of particles between 25 and 63 microns was 65% by volume.

Example 8

An 8.8% w/w polymer-in-oil oil phase (Oil Phase) was prepared by dissolving 8.5 grams of 50:50 poly(lactic-co-glycolic acid) (PLGA) (Resomer Select 5050 DLG 2A, Lot number LP1487, Evonik Corp.) in 88 grams of dichloromethane (DCM) and allowed to stir overnight at room temperature (~19° C.). A second solution (Water Phase) was made by dissolving 2.67 grams of poly(vinyl alcohol) (PVA) in 267 milliliters of deionized water overnight. A dilution phase was prepared by tempering deionized water to a temperature of 19° C. A screen was placed between the inlet tee and the helical apparatus with a mesh size of 120 by 500 (35 μm approximate retention). The Oil Phase was pumped through the assembly at a rate of 61 ml/min while the Water Phase was concurrently pumped through the same assembly at a rate of 160 ml/min. The resulting Reynolds number through the apparatus was laminar, falling between 168 and 2,948, which is well below the critical Reynolds number of 9,375 for this mixer. Upon leaving the helical apparatus, the emulsion was diluted using deionized water pumped at a rate of 1,200 ml/min. The particle size distribution of the emulsion was then analyzed using laser diffraction (Beckman Coulter LS 13 320). The median particle size (d50) of the emulsion was found to be 48 microns with a d10 of 21 μm and a d90 of 75 μm. The percentage of particles between 25 and 63 microns was 67% by volume.

Example 9

An 8.8% w/w polymer-in-oil oil phase (Oil Phase) was prepared by dissolving 8.5 grams of 50:50 poly(lactic-co-glycolic acid) (PLGA) (Resomer Select 5050 DLG 2A, Lot number LP1487, Evonik Corp.) in 88 grams of dichloromethane (DCM) and allowed to stir overnight at room temperature (~19° C.). A second solution (Water Phase) was made by dissolving 2.67 grams of poly(vinyl alcohol) (PVA) in 267 milliliters of deionized water overnight. A dilution phase was prepared by tempering deionized water to a temperature of 19° C. A screen was placed between the outlet of the helical apparatus and the dilution tee with a mesh size of 100 (140 μm approximate retention). The Oil Phase was pumped through the assembly at a rate of 61 ml/min while the Water Phase was concurrently pumped through the same assembly at a rate of 160 ml/min. The resulting Reynolds number through the apparatus was laminar, falling between 168 and 2,948, which is well below the critical Reynolds number of 9,375 for this mixer. Upon leaving the helical apparatus, the emulsion was diluted using deionized water pumped at a rate of 1,200 ml/min. The particle size distribution of the emulsion was then analyzed using laser diffraction (Beckman Coulter LS 13 320). The median particle size (d50) of the emulsion was found to be 62 μm with a d10 of 25 μm and a d90 of 122 μm. The percentage of particles between 25 and 63 microns was 44% by volume.

Example 10

An 8.8% w/w polymer-in-oil oil phase (Oil Phase) was prepared by dissolving 8.5 grams of 50:50 poly(lactic-co-glycolic acid) (PLGA) (Resomer Select 5050 DLG 2A, Lot number LP1487, Evonik Corp.) in 88 grams of dichloromethane (DCM) and allowed to stir overnight at room temperature (~19° C.). A second solution (Water Phase) was made by dissolving 2.67 grams of poly(vinyl alcohol) (PVA) in 267 milliliters of deionized water overnight. A dilution phase was prepared by tempering deionized water to a temperature of 19° C. A screen was placed between the inlet tee and the helical apparatus, as well as between the outlet of the helical apparatus and the dilution tee. Both screens had a mesh size of 100 (140 μm approximate retention). The Oil Phase was pumped through the assembly at a rate of 61 ml/min while the Water Phase was concurrently pumped through the same assembly at a rate of 200 ml/min. The resulting Reynolds number through the apparatus was laminar, falling between 198 and 3,482, which is well below the critical Reynolds number of 9,375 for this mixer. Upon leaving the helical apparatus, the emulsion was diluted using deionized water pumped at a rate of 1200 ml/min. The particle size distribution of the emulsion was then analyzed using laser diffraction (Beckman Coulter LS 13 320). The median particle size (d50) of the emulsion was found to be 44 microns with a d10 of 15 μm and a d90 of 69 μm. The percentage of particles between 25 and 63 microns was 68% by volume.

Example 11

An 8.8% w/w polymer-in-oil oil phase (Oil Phase) was prepared by dissolving 8.5 grams of 50:50 poly(lactic-co-glycolic acid) (PLGA) (Resomer Select 5050 DLG 2A, Lot number LP1487, Evonik Corp.) in 88 grams of dichloromethane (DCM) and allowed to stir overnight at room temperature (~19° C.). A second solution (Water Phase) was made by dissolving 2.67 grams of poly(vinyl alcohol) (PVA) in 267 milliliters of deionized water overnight. A dilution phase was prepared by tempering deionized water to a temperature of 19° C. A screen was placed between the inlet tee and the helical apparatus with a mesh size of 100 (140 μm approximate retention). The Oil Phase was pumped through the assembly at a rate of 61 ml/min while the Water Phase was concurrently pumped through the same assembly at a rate of 160 ml/min. The resulting Reynolds number through the apparatus was laminar, falling between 168 and 2,948, which is well below the critical Reynolds number of 9,375 for this mixer. Upon leaving the helical apparatus, the emulsion was diluted using deionized water pumped at a rate of 1,200 ml/min. The particle size distribution of the emulsion was then analyzed using laser diffraction (Beckman Coulter LS 13 320). The median particle size (d50) of the emulsion was found to be 51 microns with a d10 of 21 μm and a d90 of 73 μm. The percentage of particles between 25 and 63 microns was 64% by volume.

Example 12

An 8.8% w/w polymer-in-oil oil phase (Oil Phase) was prepared by dissolving 8.5 grams of 50:50 poly(lactic-co-glycolic acid) (PLGA) (Resomer Select 5050 DLG 2A, Lot number LP1487, Evonik Corp.) in 88 grams of dichloromethane (DCM) and allowed to stir overnight at room temperature (~19° C.). A second solution (Water Phase) was made by dissolving 2.67 grams of poly(vinyl alcohol) (PVA) in 267 milliliters of deionized water overnight. A dilution phase was prepared by tempering deionized water to a temperature of 19° C. A screen was placed between the inlet tee and the helical apparatus, as well as between the outlet of the helical apparatus and the dilution tee. Both screens had a mesh size of 100 (140 μm approximate retention). The Oil Phase was pumped through the assembly at a rate of 59 ml/min while the Water Phase was concurrently pumped through the same assembly at a rate of 150 ml/min. The resulting Reynolds number through the apparatus was laminar, falling between 159 and 2,788, which is well below the critical Reynolds number of 9,375 for this mixer. Upon leaving the helical apparatus, the emulsion was diluted using deionized water pumped at a rate of 1,100 ml/min. The particle size distribution of the emulsion was then analyzed using laser diffraction (Beckman Coulter LS 13 320). The median particle size (d50) of the emulsion was found to be 45 microns with a d10 of 15 μm and a d90 of 70 μm. The percentage of particles between 25 and 63 microns was 67% by volume.

Example 13

An 8.8% w/w polymer-in-oil oil phase (Oil Phase) was prepared by dissolving 8.5 grams of 50:50 poly(lactic-co-glycolic acid) (PLGA) (Resomer Select 5050 DLG 2A, Lot number LP1487, Evonik Corp.) in 88 grams of dichloromethane (DCM) and allowed to stir overnight at room temperature (~19° C.). A second solution (Water Phase) was made by dissolving 2.67 grams of poly(vinyl alcohol) (PVA) in 267 milliliters of deionized water overnight. A dilution phase was prepared by tempering deionized water to a temperature of 19° C. A screen was placed between the inlet tee and the helical apparatus, as well as between the outlet of the helical apparatus and the dilution tee. Both screens had a mesh size of 100 (140 μm approximate retention). The Oil Phase was pumped through the assembly at a rate of 51 ml/min while the Water Phase was concurrently pumped through the same assembly at a rate of 140 ml/min. The resulting Reynolds number through the apparatus was laminar, falling between 148 and 2,548, which is well below the critical Reynolds number of 9,375 for this mixer. Upon leaving the helical apparatus, the emulsion was diluted using deionized water pumped at a rate of 1,000 ml/min. The particle size distribution of the emulsion was then analyzed using laser diffraction (Beckman Coulter LS 13 320). The median particle size (d50) of the emulsion was found to be 55 microns with a d10 of 21 μm and a d90 of 84 μm. The percentage of particles between 25 and 63 microns was 55% by volume.

Example 14

An 8.8% w/w polymer-in-oil oil phase (Oil Phase) was prepared by dissolving 8.5 grams of 50:50 poly(lactic-co-glycolic acid) (PLGA) (Resomer Select 5050 DLG 2A, Lot number LP1487, Evonik Corp.) in 88 grams of dichloromethane (DCM) and allowed to stir overnight at room temperature (~19° C.). A second solution (Water Phase) was made by dissolving 2.67 grams of poly(vinyl alcohol) (PVA) in 267 milliliters of deionized water overnight. A dilution phase was prepared by tempering deionized water to a temperature of 19° C. A screen was placed between the inlet tee and the helical apparatus, as well as between the outlet of the helical apparatus and the dilution tee. Both screens had a mesh size of 100 (140 μm approximate retention). The Oil Phase was pumped through the assembly at a rate of 50 ml/min while the Water Phase was concurrently pumped through the same assembly at a rate of 120 ml/min. The resulting Reynolds number through the apparatus was laminar, falling between 129 and 2,268, which is well below the critical Reynolds number of 9,375 for this mixer. Upon leaving the helical apparatus, the emulsion was diluted using deionized water pumped at a rate of 900 ml/min. The particle size distribution of the emulsion was then analyzed using laser diffraction (Beckman Coulter LS 13 320). The median particle size (d50) of the emulsion was found to be 59 microns with a d10 of 24 μm and a d90 of 92 μm. The percentage of particles between 25 and 63 microns was 50% by volume.

Example 15

An 8.8% w/w polymer-in-oil oil phase (Oil Phase) was prepared by dissolving 8.5 grams of 50:50 poly(lactic-co-glycolic acid) (PLGA) (Resomer Select 5050 DLG 2A, Lot number LP1487, Evonik Corp.) in 88 grams of dichloromethane (DCM) and allowed to stir overnight at room temperature (~19° C.). A second solution (Water Phase) was made by dissolving 2.67 grams of poly(vinyl alcohol) (PVA) in 267 milliliters of deionized water overnight. A dilution phase was prepared by tempering deionized water to a temperature of 19° C. A screen was placed between the outlet of the helical apparatus and the dilution tee with a mesh size of 100 (140 μm approximate retention). The Oil Phase was pumped through the assembly at a rate of 61 ml/min while the Water Phase was concurrently pumped through the same assembly at a rate of 160 ml/min. The resulting Reynolds number through the apparatus was laminar, falling between 168 and 2,948, which is well below the critical Reynolds number of 9,375 for this mixer. Upon leaving the helical apparatus, the emulsion was diluted using deionized water pumped at a rate of 1,230 ml/min. The particle size distribution of the emulsion was then analyzed using laser diffraction (Beckman Coulter LS 13 320). The median particle size (d50) of the emulsion was found to be 50 microns with a d10 of 18 μm and a d90 of 81 μm. The percentage of particles between 25 and 63 microns was 59% by volume.

Example 16

An 8.8% w/w polymer-in-oil oil phase (Oil Phase) was prepared by dissolving 8.5 grams of 50:50 poly(lactic-co-glycolic acid) (PLGA) (Resomer Select 5050 DLG 2A, Lot number LP1487, Evonik Corp.) in 88 grams of dichloromethane (DCM) and allowed to stir overnight at room temperature (~19° C.). A second solution (Water Phase) was made by dissolving 2.67 grams of poly(vinyl alcohol) (PVA) in 267 milliliters of deionized water overnight. A dilution phase was prepared by tempering deionized water to a temperature of 19° C. A screen was placed between the inlet tee and the helical apparatus with a mesh size of 100 (140 μm approximate retention). The Oil Phase was pumped through the assembly at a rate of 61 ml/min while the Water Phase was concurrently pumped through the same assembly at a rate of 160 ml/min. The resulting Reynolds number through the apparatus was laminar, falling between 168 and 2,948, which is well below the critical Reynolds number of 9,375 for this mixer. Upon leaving the helical apparatus, the emulsion was diluted using deionized water pumped at a rate of 1230 ml/min. The particle size distribution of the emulsion was then analyzed using laser diffraction (Beckman Coulter LS 13 320). The median particle size (d50) of the emulsion was found to be 55 microns with a d10 of 24 μm and a d90 of 92 μm. The percentage of particles between 25 and 63 microns was 59% by volume.

Example 17

An 8.8% w/w polymer-in-oil oil phase (Oil Phase) was prepared by dissolving 8.5 grams of 50:50 poly(lactic-co-glycolic acid) (PLGA) (Resomer Select 5050 DLG 2A, Lot number LP1487, Evonik Corp.) in 88 grams of dichloromethane (DCM) and allowed to stir overnight at room temperature (~19° C.). A second solution (Water Phase) was made by dissolving 2.67 grams of poly(vinyl alcohol) (PVA) in 267 milliliters of deionized water overnight. A dilution phase was prepared by tempering deionized water to a temperature of 19° C. A screen was placed between the inlet tee and the helical apparatus, as well as between the outlet of the helical apparatus and the dilution tee. Both screens had a mesh size of 100 (140 μm approximate retention). The Oil Phase was pumped through the assembly at a rate of 61 ml/min while the Water Phase was concurrently pumped through the same assembly at a rate of 160 ml/min. The resulting Reynolds number through the apparatus was laminar, falling between 168 and 2,948, which is well below the critical Reynolds number of 9,375 for this mixer. Upon leaving the helical apparatus, the emulsion was diluted using deionized water pumped at a rate of 1,230 ml/min. The particle size distribution of the emulsion was then analyzed using laser diffraction (Beckman Coulter LS 13 320). The median particle size (d50) of the emulsion was found to be 39 microns with a d10 of 10 μm and a d90 of 62 μm. The percentage of particles between 25 and 63 microns was 68% by volume.

Examples 7-17 Summary

TABLE 3

| Example | Screen Mesh (inlet/outlet) | Total Flow Through Emulsifier (ml/min) | Measured Reynolds Number | Median (μm) | d10 (μm) | d90 (μm) | Particles between 25 um and 63 um (vol %) |
|---|---|---|---|---|---|---|---|
| 7 | 120 × 500/None | 251 | 191 | 45 | 20 | 80 | 65 |
| 8 | 120 × 500/None | 221 | 168 | 48 | 21 | 75 | 67 |
| 9 | None/100 | 221 | 168 | 62 | 25 | 122 | 44 |
| 10 | 100/100 | 261 | 198 | 44 | 15 | 69 | 68 |
| 11 | 100/None | 221 | 168 | 51 | 21 | 73 | 64 |
| 12 | 100/100 | 209 | 159 | 45 | 15 | 70 | 67 |
| 13 | 100/100 | 191 | 145 | 55 | 21 | 84 | 55 |
| 14 | 100/100 | 170 | 129 | 59 | 24 | 92 | 50 |
| 15 | None/100 | 221 | 168 | 50 | 18 | 81 | 59 |
| 16 | 100/None | 221 | 168 | 55 | 24 | 92 | 59 |
| 17 | 100/100 | 221 | 168 | 39 | 10 | 62 | 68 |

These examples show that the helical mixer can be used to make an emulsion that is appropriate for forming microspheres. Using screens on the entrance and/or exit of the helical mixer affects the resulting particle size distribution, by reducing the mean particle size distribution compared to an emulsion made without screens. Using screens was observed to result in a tighter particle size distribution and more material in the desired particle size range (25-63 μm) than without screens. In these examples the volume percent of microspheres with the desired particle size distribution is less than or equal to 68%.

D. Examples 18-30

Examples 18-30 use a triple helical mixer. Three identical, intertwined, right-handed helical mixers, shown in FIG. 7, for the preparation of polymer microspheres were built out of three pieces of 0.75-inch outer diameter, 0.065-inch wall 316L stainless steel tubing, each piece of tubing was wound around one another in a characteristic right-handed triple helix. The length of the tubing was sufficient so that each helix was twisted into one complete coil (i.e. a projection onto a plane perpendicular to the axis would yield a complete circle). Each individual helix has a helical length of 12.16 inches and a mean diameter of 0.885 inches, with 45 degree 0.75-inch sanitary elbows welded to each end. The three mixers were attached together by a 2.5-inch diameter mounting plate near each end of the assembly. The complete apparatus has an overall length of 15.5 inches and a diameter of 2.7 inches at the widest point. For the following examples, one, two, or three of the helices were connected to two peristaltic pumps using ¼" tubing and compression fittings, for the introduction of two unmixed liquid phases. When a single helix was used, a tee was placed after the outlet for the introduction of a liquid dilution phase. When multiple helices were used, the mixer outlets were first recombined using ¼" tubing and compression fittings, then fed into a tee for the introduction of a liquid dilution phase.

Example 18 (No Beads)

An emulsion was made using the emulsifier described above without packing with beads. An 8.8% w/w polymer-in-oil phase (Oil Phase) was prepared by dissolving 25.5 grams of 50:50 poly(lactic-co-glycolic acid) (PLGA) (Resomer Select 5050 DLG 2A, Lot number LP1321, Evonik Corp.) in 265.5 grams of dichloromethane (DCM). The solution was allowed to stir overnight at room temperature (~19° C.). A second phase, the Water Phase, was prepared by dissolving 8 grams of poly(vinyl alcohol) (PVA) in 800 grams of deionized water. The solution was stirred for one hour at 60° C. then stirred overnight at room temperature. A dilution water phase was made by setting the temperature of a vessel containing deionized water to 19° C. One of the three helical mixers, having 100 mesh screens (140 μm approximate retention) on both the inlet and outlet, was used. Approximately 140 ml of the Oil Phase and 330 ml of the Water Phase were pumped simultaneously upwards, against gravity, through the apparatus at rates of 9 ml/min and 21 ml/min, respectively. The resulting Reynolds number through the apparatus was laminar, falling between 2 and 40. The outgoing emulsion was met with the dilution water phase at a flowrate of 168 ml/min. Laser diffraction (Beckman Coulter LS 13 320) was used to analyze the particle size distribution of the resulting emulsion. The volumetric median particle size was found to be 169 μm with a d10 of 79 μm and d90 of 300 μm.

This example shows that the helical mixer can be used to make an emulsion that is appropriate for forming microspheres, at a larger microsphere scale than with the previous examples. The particle size distribution had only 4.3% of the particles in the desired 25 to 63 μm range.

Example 19 (No Beads, Faster Flow)

This example is similar to Example 18, except that the flow through the helical mixer is faster. An 8.8% w/w polymer-in-oil oil phase (Oil Phase) was prepared by dissolving 51 grams of 50:50 poly(lactic-co-glycolic acid) (PLGA) (Resomer Select 5050 DLG 2A, Lot number LP1321, Evonik Corp.) in 528 grams of dichloromethane (DCM). The solution was allowed to stir overnight at room temperature (~19° C.). A second phase, the Water Phase, was prepared by dissolving 8 grams of poly(vinyl alcohol) (PVA) in 800 grams of deionized water. The solution was stirred for one hour at 60° C. then stirred overnight at room temperature. A dilution water phase was made by setting the temperature of a vessel containing deionized water to 19° C. One of the three helical mixers, having 100 mesh screens (140 μm approximate retention) on both the inlet and outlet, was used. Approximately 120 ml of the Oil Phase and 400 ml of the Water Phase were pumped simultaneously upwards, against gravity, through the helical mixer at rates of 61 ml/min and 186 ml/min, respectively. The resulting Reynolds number through the apparatus was laminar, falling between 19 and 332. The outgoing emulsion was met with the dilution water phase at a flowrate of 542 ml/min. Laser diffraction (Beckman Coulter LS 13 320) was used to analyze the particle size distribution of the resulting emulsion. The volumetric median particle size was found to be 67.52 μm with a d10 of 29.6 μm and d90 of 74.5 μm.

This example shows that the helical mixer can be used to make an emulsion that is appropriate for forming microspheres, at a larger microsphere scale. The particle size distribution was better than the previous example, with 36% of the particles in the desired range.

Example 20 (Large Beads)

For this example, a helical mixer packed with 2 mm glass beads was used to create an emulsion that can be used to make microspheres. Using packing allows reduced flow rates, which reduce convection currents, resulting in a less turbulent environment for the emulsion droplets and the fragile physiologically active substances An 8.8% w/w polymer-in-oil oil phase (Oil Phase) was prepared by dissolving 51 grams of 50:50 poly(lactic-co-glycolic acid) (PLGA) (Resomer Select 5050 DLG 2A, Lot number LP1321, Evonik Corp.) in 529 grams of dichloromethane (DCM) and allowed to stir overnight at room temperature (~19° C.). A second phase, the Water Phase, was prepared by dissolving 32 grams of poly(vinyl alcohol) (PVA) in 3,200 grams of deionized water. The solution was stirred for one hour at 60° C. then stirred overnight at room temperature. A dilution water phase was made by setting the temperature of a vessel containing deionized water to 19° C. One of the three helical mixers was packed with 2-millimeter diameter glass beads and 100 mesh screens (140 μm approximate retention) were placed on both the inlet and outlet. Approximately 50 ml of the Oil Phase and 200 ml of the Water Phase were pumped simultaneously upwards, against gravity, through the helical mixer apparatus at rates of 37 ml/min and 180 ml/min, respectively. The resulting Reynolds number through the apparatus was laminar, falling between 2 and 37. Laser diffraction (Beckman Coulter LS 13 320) was used to analyze the particle size distribution of the resulting emulsion. The volumetric median particle size was found to be 41.83 μm with a d10 of 14.17 μm and d90 of 56.38 μm.

The particle size distribution was better than the previous example, with 81.6% of the particles in the desired range, suggesting that packing the emulsifier with beads has a positive effect on emulsion quality.

Example 21 (Large Beads)

This example is similar to Example 20, except that the flow through the mixer was adjusted. An 8.8% w/w polymer-in-oil oil phase (Oil Phase) was prepared by dissolving 51 grams of 50:50 poly(lactic-co-glycolic acid) (PLGA) (Resomer Select 5050 DLG 2A, Lot number LP1321, Evonik Corp.) in 529 grams of dichloromethane (DCM) and allowed to stir overnight at room temperature (~19° C.), resulting in approximately 400 mL of Oil Phase. A second phase, the Water Phase, was prepared by dissolving 32 grams of poly(vinyl alcohol) (PVA) in 3200 grams of deionized water. The solution was stirred for one hour at 60° C. then stirred overnight at room temperature. A dilution water phase was made by setting the temperature of a vessel containing deionized water to 19° C. One of the three helical mixers was packed with 2-millimeter diameter glass beads and 100 mesh screens (140 μm approximate retention) were placed on both the inlet and outlet. Approximately 50 ml of the Oil Phase and 440 ml of the Water Phase were pumped simultaneously upwards, against gravity, through the helical mixer apparatus at rates of 37 ml/min and 220 ml/min, respectively. The resulting Reynolds number through the apparatus was laminar, falling between 2.5 and 44. Laser diffraction (Beckman Coulter LS 13 320) was used to analyze the particle size distribution of the resulting emulsion. The volumetric median particle size was found to be 40.89 μm with a d10 of 13.35 μm and d90 of 56.58 μm.

The particle size distribution was similar to Example 20, with 79.2% of the particles in the desired range.

Example 22 (Small Beads)

For examples 22-26, the emulsifier was filled with smaller beads (~327 μm median diameter), to determine if further improvements could be made to the particle size distribution.

An 8.8% w/w polymer-in-oil oil phase (Oil Phase) was prepared by dissolving 51 grams of 50:50 poly(lactic-co-glycolic acid) (PLGA) (Resomer Select 5050 DLG 2A, Lot number LP1321, Evonik Corp.) in 529 grams of dichloromethane (DCM) and allowed to stir overnight at room temperature (~19° C.). A second phase, the Water Phase, was prepared by dissolving 32 grams of poly(vinyl alcohol) (PVA) in 3,200 grams of deionized water. The solution was stirred for one hour at 60° C. then stirred overnight at room temperature. A dilution water phase was made by setting the temperature of a vessel containing deionized water to 19° C. One of the three helical mixers was packed with 327 μm borosilicate glass beads (MO-SCI Health Care, GL0179B5/300-355) and 100 mesh screens (140 μm approximate retention) were placed on both the inlet and outlet. Approximately 50 ml of the Oil Phase and 100 ml the Water Phase were pumped simultaneously upwards, against gravity, through the packed bed apparatus at rates of 9 ml/min and 21 ml/min, respectively. The resulting Reynolds number through the apparatus was laminar, falling between 0.05 and 0.83. The outgoing emulsion was met with the dilution water phase at a flowrate of 168 ml/min. Laser diffraction (Beckman Coulter LS 13 320) was used to analyze the particle size distribution of the resulting emulsion.

The volumetric median particle size was found to be 40.49 μm with a d10 of 24.7 μm and d90 of 50.57 μm. The distribution was better than Example 21, with 90% of the particles in the desired range, suggesting that using smaller beads and slower flow rates in the emulsifier, increases the quality of the resulting emulsion.

Example 23 (Small Beads PEG-Insulin Microspheres)

For this example, a small batch of drug-loaded microspheres was made with PEG-insulin using the same emulsion step as Example 22. A 10% w/w polymer-in-oil oil phase (Oil Phase) was prepared by dissolving 8.5 grams of 50:50 poly(lactic-co-glycolic acid) (PLGA) (Resomer Select 5050 DLG 2A, Lot number LP1321, Evonik Corp.) in 88 grams of dichloromethane (DCM) along with 1.5 grams of PEGylated Insulin Drug Substance (Lot 102516). The solution was stirred overnight at room temperature (~19° C.). A second phase, the Water Phase, was prepared by dissolving 2.67 grams of poly(vinyl alcohol) (PVA) in 267 grams of deionized water. The solution was stirred for one hour at 60° C. then stirred overnight at room temperature. A dilution water phase was made by setting the temperature of a vessel containing deionized water to 19° C. One of the three helical mixers was packed with 327 μm borosilicate glass beads (MO-SCI Health Care, GL0179B5/300-355) and 100 mesh screens (140 μm approximate retention) were placed on both the inlet and outlet.

The Oil Phase and Water Phase were pumped simultaneously upwards, against gravity, through the packed helical apparatus at rates of 9 ml/min and 21 ml/min, respectively. The resulting Reynolds number through the apparatus was laminar, falling between 0.05 and 0.83. The emulsion leaving the apparatus was met with the dilution water phase at a flowrate of 168 ml/min. Flow through the helical mixer slowed after approximately half of the Oil and Water Phases had been passed through the mixer. The flow eventually stopped, due to apparent clogging. The remaining Oil Phase and Water Phase were pumped through a different but identical helical mixer. Once all of the remaining Oil Phase had been passed through the mixer, the emulsion was held in the primary tank while stirring for 30 minutes. After the 30-minute hold, the contents of the primary tank were transferred to a secondary tank at a flowrate of 24 ml/min. Dilution water, in line with the emulsion transfer, was pumped at a rate of 115 ml/min.

Once the volume in the secondary tank reached 0.5 liters, cross-flow filtration (CFF) was started using a 5 μm ceramic membrane. The microspheres were recirculated through the CFF membrane at a rate of 1.9 L/min with the permeate waste exiting the CFF membrane at 139 ml/min, in order to maintain the volume in the secondary tank at 0.5 L. Once the entirety of the primary tank had been transferred to the secondary tank, the temperature of the tank jackets was increased to 25° C. and the dilution water flowrate was reduced to 25 ml/min. Additionally, the permeate flowrate was reduced to 25 ml/min for the diafiltration step. This process was continued until a total of six diavolumes, or 3 liters, had been exchanged and then the temperature of the secondary tank was increased and held at 35° C. for two hours. At the end of the temperature hold, the microspheres were cooled to 4° C. before being loaded onto the 25 μm screen of the filter dryer. The secondary tank was rinsed with 600 ml of chilled Milli-Q water and this rinse water was also added to the filter dryer. The filter dryer was vibrated in the forward direction while loading, and the liquid permeate was drained off, leaving the microsphere product on the screen. An air sweep of 5 sLpm was applied to the filter dryer overnight to facilitate in drying of the microspheres. After approximately 24 hours, the microspheres were harvested from the screen.

The total harvested mass was 1.56 grams of product. This low yield was likely due to losses caused by the clogging of the helical mixer. The clogging might be because the small glass bead size is increasing pressure through the helical mixer, which the pumps cannot overcome. Laser diffraction (Beckman Coulter LS 13 320) was used to analyze the particle size distribution of the final microspheres. The volumetric median particle size was found to be 43.3 μm with a d10 of 31.0 μm and d90 of 53.7 μm.

Example 24 (PTFE Pump Heads)

Pumps were used which were rated to provide up to 100 psi to overcome the back pressure experienced during the previous examples. An 8.8% w/w polymer-in-oil oil phase (Oil Phase) was prepared by dissolving 8.5 grams of 50:50 poly(lactic-co-glycolic acid) (PLGA) (Resomer Select 5050 DLG 2A, Lot number LP1321, Evonik Corp.) in 88 grams of dichloromethane (DCM) and allowed to stir overnight at room temperature (~19° C.). A second phase, the Water Phase, was prepared by dissolving 8 grams of poly(vinyl alcohol) (PVA) in 800 grams of deionized water. The solution was stirred for one hour at 60° C., then stirred overnight at room temperature. A dilution water phase was made by setting the temperature of a vessel containing deionized water to 19° C. One of the three helical mixers was packed with 327 μm borosilicate glass beads (MO-SCI Health Care, GL0179B5/300-355) and 100 mesh screens (140 μm approximate retention) were placed on both the inlet and outlet. The Oil Phase and the Water Phase were pumped simultaneously upwards, against gravity, through the packed bed apparatus at rates of 9 ml/min and 21 ml/min, respectively. The resulting Reynolds number through the apparatus was laminar, falling between 0.05 and 0.83. The pumps used for this example were able to create up to 100 psi of pressure to overcome the back pressure experienced during the previous examples. The outgoing emulsion was met with the dilution water phase at a flowrate of 168 ml/min. The pressure was measured near the junction of the Oil and Water Phases at the inlet of the helical mixer and was found to be 35 psi. Laser diffraction (Beckman Coulter LS 13 320) was used to analyze the particle size distribution of the resulting emulsion. The volumetric median particle size was found to be 41.7 μm with a d10 of 13.6 μm and d90 of 48.7 μm.

The particle size distribution had a high percentage in the targeted range, with 88.1% of the particles in the targeted range. The pumps were able to provide enough pressure to overcome the 35 psi of backpressure created by the smaller packing.

Example 25 (PTFE Pump Heads, Slower Flow Rates)

Pumps were used which were able to provide up to 100 psi in order to overcome the back pressure experienced during the previous examples. In addition, lower flow rates (half of the flowrates used in Example 24) were used to reduce the pressure drop through the packed helical mixer.

An 8.8% w/w polymer-in-oil oil phase (Oil Phase) was prepared by dissolving 8.5 grams of 50:50 poly(lactic-co-glycolic acid) (PLGA) (Resomer Select 5050 DLG 2A, Lot number LP1321, Evonik Corp.) in 88 grams of dichloromethane (DCM) and allowed to stir overnight at room temperature (~19° C.). A second phase, the Water Phase, was prepared by dissolving 8 grams of poly(vinyl alcohol) (PVA) in 800 grams of deionized water. The solution was stirred for one hour at 60° C. then stirred overnight at room temperature. A dilution water phase was made by setting the temperature of a vessel containing deionized water to 19° C. One of the three helical mixers was packed with 327 μm borosilicate glass beads (MO-SCI Health Care, GL0179B5/300-355) and 100 mesh screens (140 μm approximate retention) were placed on both the inlet and outlet. The Oil Phase and the Water Phase were pumped simultaneously upwards, against gravity, through the packed bed apparatus at rates of 4.5 ml/min and 10.5 ml/min, respectively. The resulting Reynolds number through the apparatus was laminar, falling between 0.02 and 0.42. The pumps used for this example were able to create up to 100 psi of pressure to overcome the back pressure experienced during the previous examples. The outgoing emulsion was met with the dilution water phase at a flowrate of 84 ml/min. The pressure was measured near the junction of the Oil and Water Phases at the inlet of the helical mixer and was found to be 25 psi. Laser diffraction (Beckman Coulter LS 13 320) was used to analyze the particle size distribution of the resulting emulsion. The volumetric median particle size was found to be 41.7 µm with a d10 of 26.2 µm and d90 of 50.3 µm.

The particle size distribution had a high percentage (90.6%) of the particles in the desired range. This batch had slightly better particle size distribution than the previous example, possibly due to the reduction in flowrate and backpressure.

Example 26 (PTFE Pump Heads, Slower Flow Rates)

Pumps were used which were able to provide up to 100 psi in order to overcome the back pressure experienced during the previous examples. In addition, lower flow rates (one quarter of the flow rates used in Example 24) were used to reduce pressure.

An 8.8% w/w polymer-in-oil oil phase (Oil Phase) was prepared by dissolving 8.5 grams of 50:50 poly(lactic-co-glycolic acid) (PLGA) (Resomer Select 5050 DLG 2A, Lot number LP1321, Evonik Corp.) in 88 grams of dichloromethane (DCM) and allowed to stir overnight at room temperature (~19° C.). A second phase, the Water Phase, was prepared by dissolving 8 grams of poly(vinyl alcohol) (PVA) in 800 grams of deionized water. The solution was stirred for one hour at 60° C. then stirred overnight at room temperature. A dilution water phase was made by setting the temperature of a vessel containing deionized water to 19° C. One of the three helical mixers was packed with borosilicate glass beads (MO-SCI Health Care, GL0179B5/300-355) and 100 mesh screens (140 µm approximate retention) were placed on both the inlet and outlet. The Oil Phase and the Water Phase were pumped simultaneously upwards, against gravity, through the packed bed apparatus at rates of 2.25 ml/min and 5.25 ml/min, respectively. The resulting Reynolds number through the apparatus was laminar, falling between 0.01 and 0.21. The pumps used for this example were able to create up to 100 psi of pressure to overcome the back pressure experienced during the previous examples. The outgoing emulsion was met with the dilution water phase at a flowrate of 42 ml/min. The pressure was measured near the junction of the Oil and Water Phases at the inlet of the helical mixer and was 25 psi. Laser diffraction (Beckman Coulter LS 13 320) was used to analyze the particle size distribution of the resulting emulsion. The volumetric median particle size was found to be 45.8 µm with a d10 of 29.44 µm and d90 of 54.9 µm.

The particle size distribution had a high percentage (92.6%) in the targeted range. This batch had slightly better particle size distribution than the previous example, possibly due to the reduction in flowrate and backpressure. Although the slower flowrates seem to reduce pressure and improve particle size distribution, slower flow rates also increase process time.

Example 27 (Mixed Beads)

This example used half 1 mm beads and half 327 µm beads to reduce the pressure drop through the mixer. An 8.8% w/w polymer-in-oil oil phase (Oil Phase) was prepared by dissolving 8.5 grams of 50:50 poly(lactic-co-glycolic acid) (PLGA) (Resomer Select 5050 DLG 2A, Lot number LP1321, Evonik Corp.) in 88 grams of dichloromethane (DCM) and allowed to stir overnight at room temperature (~19° C.). A second phase, the Water Phase, was prepared by dissolving 8 grams of poly(vinyl alcohol) (PVA) in 800 grams of deionized water. The solution was stirred for one hour at 60° C. then stirred overnight at room temperature. A dilution water phase was made by setting the temperature of a vessel containing deionized water to 19° C. One of the three helical mixers was packed with 58.89 g of 1 mm borosilicate glass beads (MO-SCI Health Care, GL01915B/1000) then the remaining mixer volume was filled with 327 µm borosilicate glass beads (MO-SCI Health Care, GL0179B5/300-355) and 100 mesh screens (140 µm approximate retention) were placed on both the inlet and outlet. The Oil Phase and the Water Phase were pumped simultaneously upwards, against gravity, through the packed bed apparatus at rates of 9 ml/min and 21 ml/min, respectively. The resulting Reynolds number through the apparatus was laminar, falling between 0.05 and 0.83. The outgoing emulsion was met with the dilution water phase at a flowrate of 168 ml/min. The pressure was measured near the junction of the Oil and Water Phases at the inlet of the helical mixer and was found to be 15 psi. Laser diffraction (Beckman Coulter LS 13 320) was used to analyze the particle size distribution of the resulting emulsion. The volumetric median particle size was found to be 47.7 µm with a d10 of 33.5 µm and d90 of 59.0 µm.

The particle size distribution had a high percentage (94.9%) of the particles in the desired range. This batch had slightly better particle size distribution than the previous example, possibly due to the reduction in backpressure. This example also used higher flow rates which is advantageous because it would result in shorter process times and still be able to achieve better particle size distribution than Example 26.

Example 28 (PEG-Insulin Microspheres)

A batch of microspheres was made with PEG-insulin using the same emulsion step as Example 27. A 10% w/w polymer-in-oil oil phase (Oil Phase) was prepared by dissolving 8.5 grams of 50:50 poly(lactic-co-glycolic acid) (PLGA) (Resomer Select 502H, Lot number 577, Evonik Corp.) in 88 grams of dichloromethane (DCM) along with 1.5 grams of PEGylated Insulin Drug Substance (Lot 102516). The solution was allowed to stir overnight at room temperature (~19° C.). A second phase, the Water Phase, was prepared by dissolving 2.67 grams of poly(vinyl alcohol) (PVA) in 267 grams of deionized water. The solution was stirred for one hour at 60° C. then stirred overnight at room temperature. A dilution water phase was made by setting the temperature of a vessel containing deionized water to 19° C. One of the three helical mixers was packed with 39.45 g of 1 mm borosilicate glass beads (MO-SCI Health Care, GL01915B/1000) then the remaining mixer volume was filled with 327 µm borosilicate glass beads (MO-SCI Health Care, GL0179B5/300-355) and 100 mesh screens (140 µm approximate retention) were placed on both the inlet and outlet. The Oil Phase and Water Phase were pumped simultaneously upwards, against gravity, through the packed bed apparatus at rates of 9 ml/min and 21 ml/min, respectively. The resulting Reynolds number through the apparatus was laminar, falling between 0.05 and 0.83. The outgoing emulsion was met with the dilution water phase at a flowrate of 168 ml/min. The maximum pressure through the mixer was measured at the inlet of the mixer and found to be 20 psi.

Once all of the remaining Oil Phase had been passed through the mixer, the emulsion was held in the primary tank while stirring for 30 minutes. After the 30-minute hold, the contents of the primary tank were transferred to a secondary tank at a flowrate of 24 ml/min. Dilution water, in line with the emulsion transfer, was pumped at a rate of 115 ml/min. Once the volume in the secondary tank reached 0.5 liters, cross-flow filtration (CFF) was started using a 5 µm ceramic membrane. The microspheres were recirculated through the CFF membrane at a rate of 1.9 L/min with the permeate waste exiting the CFF membrane at 139 ml/min, in order to maintain the volume in the secondary tank at 0.5 L. Once the entirety of the primary tank had been transferred to the secondary tank, the temperature of the tank jackets was increased to 25° C. and the dilution water flowrate was reduced to 25 ml/min. Additionally, the permeate flowrate was reduced to 25 ml/min for the diafiltration step. This process was continued until a total of six diavolumes, or 3 liters, had been exchanged and then the temperature of the secondary tank was increased and held at 35° C. for two hours.

At the end of the temperature hold, the microspheres were cooled to 4° C. before being loaded onto the 25 µm screen of the filter dryer. The secondary tank was rinsed with 600 ml of chilled 0.5% sodium bicarbonate and this rinse was added to the filter dryer. The filter dryer was vibrated in the forward direction while loading and the liquid was drained off leaving the microspheres on the screen. An air sweep of 5 sLpm was applied to the filter dryer overnight to facilitate in drying of the microspheres. After approximately 24 hours, the microspheres were harvested from the screen.

The total harvested mass was 6.06 grams of product. This yield was higher than Example 23, likely due to the elimination of clogging for this batch. Laser diffraction (Beckman Coulter LS 13 320) was used to analyze the particle size distribution of the resulting emulsion. The volumetric median particle size was found to be 47.9 µm with a d10 of 38.2 µm and d90 of 57.5 µm. The volume percent of particles in the desired range of 25-65 µm was 97.6%.

Example 29 (Scaled Up)

To demonstrate scalability, Example 22 was repeated at a larger scale, using three helices in parallel instead of a single helix. An 8.8% w/w polymer-in-oil oil phase (Oil Phase) was prepared by dissolving 51 grams of 50:50 poly(lactic-co-glycolic acid) (PLGA) (Resomer Select 5050 DLG 2A, Lot number LP1321, Evonik Corp.) in 528 grams of dichloromethane (DCM. The solution was allowed to stir overnight at room temperature (~19° C.). A second phase, the Water Phase, was prepared by dissolving 32 grams of poly(vinyl alcohol) (PVA) in 3210 grams of deionized water. The solution was stirred for one hour at 60° C. then stirred overnight at room temperature. 110 grams of DCM was then added to the Water phase and allowed to stir in a sealed bottle overnight. A dilution water phase was made by setting the temperature of a vessel containing deionized water to 19° C. Three helical mixers were packed with borosilicate glass spheres (MO-SCI Health Care, GL0179B5/300-355) and 100 mesh screens (140 µm approximate retention) were placed on each inlet and outlet. Approximately 232 ml of the Oil Phase and 783 ml of the Water Phase were pumped simultaneously upwards, against gravity, through the packed helical apparatus at rates of 8 ml/min and 27 ml/min, respectively. The resulting Reynolds number through the apparatus was laminar, falling between 0.02 and 0.32. The outgoing emulsion was met with the dilution water phase at a flowrate of 166 ml/min. Maximum pressure observed was 30 psi and no reduction in flow rate was observed during the emulsion step. Laser diffraction (Beckman Coulter LS 13 320) was used to analyze the particle size distribution of the resulting emulsion. The volumetric median particle size was found to be 45.3 µm with a d10 of 32.0 µm and d90 of 55.8 µm. The volume percent of particles in the desired range of 25-65 µm was 91.85%.

This example demonstrated that the emulsification process could be scaled up to make an emulsion sufficient to make 30 grams of microspheres, using the same process as Example 22, which made an emulsion sufficient to make 10 grams of microspheres. This example showed that a triple helix could be used to scale up the amount of emulsion produced without increasing the space occupied by the emulsifier. The three helices occupy roughly the same space as a single helix. The particle size distribution was similar for this example and Example 22, which suggests that the emulsification is scalable.

Example 30 (Screens for Classification)

In this example, the emulsion was performed at a reduced temperature (~4° C.) compared to the other examples, to determine how this could affect the particle size distribution. In addition, a 200×1150 mesh screen (10 µm approximate retention) with recirculating flow from the secondary stirred tank was used, instead of a ceramic 5 µm cross-flow filtration membrane, for both the concentration step and the diafiltration step. After concentration and diafiltration, the microspheres, with recirculating flow from the stirred tank, were passed through a 150 mesh screen (100 µm approximate retention) and into the filter dryer. This step eliminates any microspheres or aggregates that are larger than 100 µm and collects only the desired microsphere product. This example demonstrated that a plurality of screens with recirculating flow from a stirred tank, can be used to classify the microspheres based on their particle size distribution and result in better control of the microparticles produced.

An 8.8% w/w polymer-in-oil oil phase (Oil Phase) was prepared by dissolving 8.5 grams of 50:50 poly(lactic-co-glycolic acid) (PLGA) (Resomer Select 502H, Lot number 577, Evonik Corp.) in 88 grams of dichloromethane (DCM). The solution was allowed to stir overnight at room temperature (~19° C.) until dissolved, then stored overnight at 2-8° C. A second phase, the Water Phase, was prepared by dissolving 2.67 grams of poly(vinyl alcohol) (PVA) in 267 grams of deionized water. The solution was stirred for one hour at 60° C. then stirred at room temperature until dissolved and stored overnight at 2-8° C. A dilution water phase was made by setting the temperature of a vessel containing deionized water to 19° C. One of the three helical mixers was packed with 39.47 g of 1 mm borosilicate glass beads (MO-SCI Health Care, GL01915B/1000) then the remaining volume within the mixer was filled with 327 µm borosilicate glass beads (MO-SCI Health Care, GL0179B5/300-355), 100 mesh screens (140 µm approximate retention) were placed on both the inlet and outlet, and the packed helical mixer was stored overnight at 2-8° C. The Oil Phase and Water Phase were pumped simultaneously upwards, against gravity, through the packed bed apparatus at rates of 9 ml/min and 21 ml/min, respectively. The outgoing emulsion was met with the dilution water phase at a flowrate of 168 ml/min. The maximum pressure through the mixer was 20 psi.

Once the entirety of the Oil Phase had been passed through the mixer, the emulsion was held in the primary tank while stirring for 30 minutes. After the 30-minute hold, the contents of the primary tank were transferred to a secondary tank at a flowrate of 24 ml/min. Dilution water, in line with the emulsion transfer, was pumped at a rate of 115 ml/min. Once the volume in the secondary tank reached 0.5 liters, the cross-flow filtration (CFF) step was started. The microspheres were recirculated through the straight run of a tee at a rate of 1.9 L/min. A 200×1150 mesh screen (10 µm approximate retention) was placed on the branch of the tee and the waste permeate flow rate was controlled via diaphragm valve at a rate of 139 ml/min in order to maintain the fluid volume in the secondary tank at 0.5 L. Once the entirety of the primary tank was transferred to the secondary tank, the temperature of the tank jackets was increased to 25° C. and the dilution water flow rate was reduced to 25 ml/min. Additionally, the permeate flowrate was reduced to 25 ml/min for the entirety of the diafiltration step. A total of six diavolumes were completed and then the jacket of the secondary tank was increased to 35° C. and held for 2 hours.

At the end of the temperature hold, the microspheres were cooled to 4° C. and then classified by size, by recirculating through the straight run of a tee at a rate of 1.9 L/min. A 150 mesh screen (100 µm approximate retention) was placed on the branch of the tee and the product permeate flow rate was controlled via diaphragm valve and allowed to flow at a rate of 500 ml/min onto the 25 µm screen of the filter dryer. Four liters of water was concurrently added to the tank at a rate of 500 ml/min. Once microspheres were no longer observed in the secondary tank, the material in the filter dryer was rinsed with 600 ml of chilled 0.5% sodium bicarbonate. The filter dryer vibrated in the forward direction while loading and the liquid was drained off leaving the microsphere product on the screen. An air sweep of 5 sLpm was applied to the filter dryer overnight to facilitate in drying of the microspheres. After approximately 24 hours, the microspheres were harvested from the screen. The total harvested mass was 4.5 grams of product. Laser diffraction (Beckman Coulter LS 13 320) was used to analyze the particle size distribution of the resulting emulsion. The volumetric median particle size was 44.6 µm with a d10 of 27.9 µm and d90 of 56.3 µm. The volume percent of particles in the desired range of 25-65 µm was 92%.

The particle size distribution of the emulsion was not significantly different than when the emulsion was performed at room temperature, so the cold emulsion was not observed to significantly affect the particle size distribution. The volumetric median particle size after classification with the screens was 44.8 µm with a d10 of 32.9 µm and d90 of 54.5 µm. The volume percent of particles in the desired range of 25-65 µm was 96%. This example demonstrated that screens can be used for cross-flow filtration instead of the ceramic membrane and have the added advantage that they can be used to eliminate undersized particles, oversized particles, aggregates, or unwanted foreign material at the same time. Different screens sizes could be used to select a desired size distribution of the final product.

E. Examples 31-33

Figure 6:
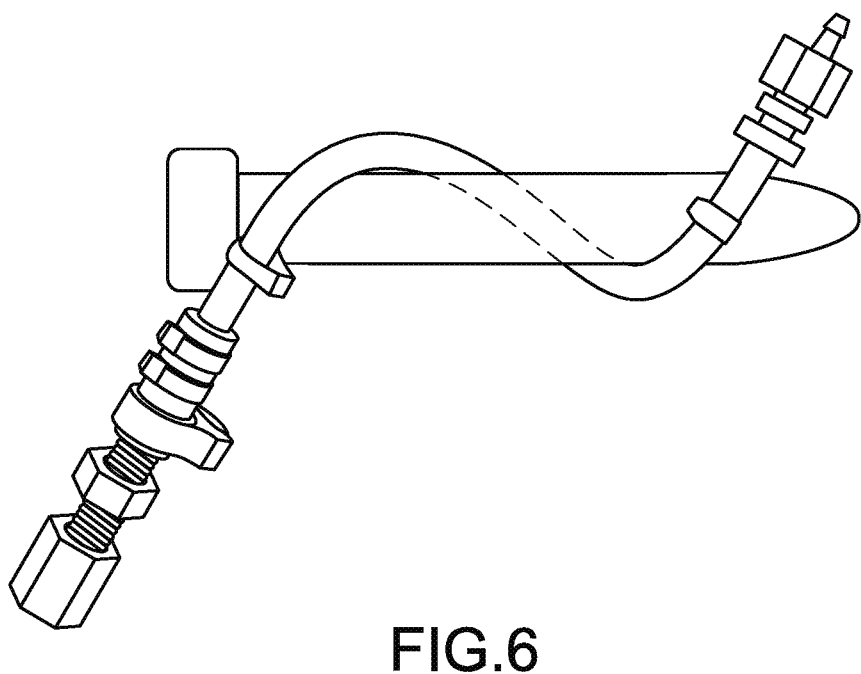
FIG. 6 shows a helical mixer according to embodiments of the present technology.

Examples 31-33 use a helical mixer. The helical mixer, shown in FIG. 6, for the preparation of polymer microspheres was created by wrapping a 6-inch piece of ¼" PTFE tubing (3/16" inner diameter) around a 0.62-inch cylinder for a total of 1 complete coil. The resulting helix has a mean diameter of 0.9 inches and a helix angle of 47 degrees. The helix was then packed with borosilicate beads with an average diameter of 327 microns. Each end of the helix was capped with a 100 mesh screen. The helical apparatus was connected to a peristaltic pump and oriented vertically in such a way that the net fluid flow was up, against gravity, then used during the following experiments.

Example 31 (GLP-1 Microspheres)

A 10% w/v polymer-in-oil phase (Oil Phase) was prepared by dissolving 1.275 grams of 50:50 poly(D,L-lactide-co-glycolide) (PLGA) (Resomer RG 502, Lot number D140800505, Evonik Corp.)+0.425 grams of 50:50 PLGA (Resomer RG 504, Lot number DBCBS4537V, Sigma Aldrich)+0.3 grams of GLP-1 protein PEGylated with a 5K PEG, in 26.6 grams of dichloromethane (DCM) and allowed to stir until dissolved at room temperature (~19° C.). Next, 360 microliters of a 50 mg/ml pamoic acid solution, prepared in N-Dimethylformamide (DMF), was added and stirred for 20 more minutes. A second solution (Water Phase) was made by dissolving 10 grams of poly(vinyl alcohol) (PVA) in 1000 milliliters of deionized water. Twenty-five milliliters of the PVA solution was added to 10 ml of the oil phase, stirred to form a course emulsion, and pumped through the helical apparatus at a rate of 3.8 ml/min. The resulting Reynolds number through the apparatus was laminar, falling between 0.07 and 0.13. Microspheres were collected in 1000 ml of a 7.2% w/v NaCl solution stirring at 200 rpm. The microsphere product was analyzed for drug loading and encapsulation efficiency using HPLC. GLP-1 drug was found to be 11.9% by mass with an encapsulation efficiency of 95%. The particle size distribution of the microspheres was analyzed using laser diffraction (Beckman Coulter LS 13 320). The volumetric median particle size of the microspheres in the primary solution was 39 µm with a d10 of 29 µm and a d90 of 47 µm.

Example 32 (GLP-1 and Insulin Microspheres)

A 10% w/v polymer-in-oil phase (Oil Phase) was prepared by dissolving 0.17 grams of 50:50 poly(D,L-lactide-co-glycolide) (PLGA) (Resomer RG 502, Lot number D140800505, Evonik Corp.)+0.015 grams of a 5K PEGylated insulin+0.015 grams of a 5K PEGylated GLP-1, in 1.995 grams of dichloromethane (DCM)+0.52 grams of benzyl alcohol, and allowed to stir until dissolved at room temperature (~19° C.). Next, 18 microliters of a 50 mg/ml pamoic acid solution, prepared in N-Dimethylformamide (DMF), was added and stirred for 20 more minutes. A second solution (Water Phase) was made by dissolving 10 grams of poly(vinyl alcohol) (PVA) in 1000 milliliters of deionized water. Five milliliters of the PVA solution was added to the oil phase, stirred to form a course emulsion, and pumped through the helical apparatus at a rate of 3.8 ml/min. The resulting Reynolds number through the apparatus was laminar, falling between 0.07 and 0.13. Microspheres were collected in 200 milliliters of a 3.6% w/v NaCl solution stirring at 120 rpm. After 2 hours, the microsphere suspension was diluted by adding 400 milliliters of 3.6% w/v NaCl and let stirring at 180 rpm for 1 hour. Next, the microspheres were centrifuged at 33 g for 5 minutes and washed with Milli-Q water. The microsphere product was analyzed for drug loading using HPLC. PEGylated GLP-1 loading was found to be 4.9% by mass. PEGylated insulin loading was found to be 6.9% by mass. The particle size distribution of the microspheres was analyzed using laser diffraction (Beckman Coulter LS 13 320). The volumetric median particle size of the microspheres was 21 µm with a d10 of 14 µm and a d90 of 27 µm.

Example 33 (Microspheres with GLP-1 and Two Different Polymers)

Two different oil phases were prepared, A and B. Oil phase A was prepared by dissolving 0.85 grams of 50:50 poly(D,L-lactide-co-glycolide) (PLGA) (Resomer RG 502, Lot number D140800505, Evonik Corp.)+0.15 grams of a 5K PEGylated GLP-1, in 13.3 grams of dichloromethane (DCM), and allowed to stir until dissolved at room temperature (~19° C.). Next, 180 microliters of a 50 mg/ml pamoic acid solution, prepared in N-Dimethylformamide (DMF), was added and stirred for 20 more minutes.

Oil phase B was prepared by dissolving 0.6375 grams of 50:50 poly(D,L-lactide-co-glycolide) (PLGA) (Resomer RG 502, Lot number D140800505, Evonik Corp.)+0.2125 grams of 50:50 poly(D,L-lactide-co-glycolide) (PLGA) (Resomer RG 503, Lot number BCBR7837V, Evonik Corp.)+ 0.15 grams of a 5K PEGylated GLP-1, in 13.3 grams of dichloromethane (DCM), and allowed to stir until dissolved at room temperature. One hundred and eighty microliters of the 50 mg/ml pamoic acid solution was added and stirred for 20 more minutes.

The Water Phase solution was made by dissolving 10 grams of poly(vinyl alcohol) (PVA) in 1000 milliliters of deionized water. Five milliliters of each Oil Phase were mixed with 12.5 ml of the PVA solution to form a course emulsion. The course emulsion formed with Oil Phase A was first pumped through the helical apparatus at a rate of 3.8 ml/min and collected in 1000 milliliters of a 7.2% NaCl solution stirring at 200 rpm. The resulting Reynolds number through the apparatus was laminar, falling between 0.07 and 0.13. Immediately after the first course emulsion had been pumped, the second course emulsion, formed with the Oil Phase B, was pumped through the helical apparatus at the same rate, and collected in the same solution. After 2 hours, the microsphere suspension was diluted by adding 2000 milliliters of 7.2% w/v NaCl and left stirring for 1 hour. The microspheres were centrifuged at 33 g for 5 minutes and washed with Milli-Q water. The microsphere product was analyzed for drug loading using HPLC. PEGylated GLP-1 loading was found to be 12.8% by mass. The particle size distribution of the microspheres was analyzed using laser diffraction (Beckman Coulter LS 13 320). The volumetric median particle size of the microspheres was 42 µm with a d10 of 31 µm and a d90 of 55 µm.

Examples 31-33 Summary

These examples demonstrated that the helical mixer can be used for making microspheres with different APIs and polymers. The resulting particle size distributions had a high percentage in the targeted range, and the processes used laminar flow which is less likely to cause shear stresses on fragile protein drugs and results in better, more uniform emulsions.

F. Examples 34-37

Examples 34-36 show the viability of helical mixers packed with a gradient of bead diameters. Example 37 shows the viability of producing two sets of microspheres with two different physiologically active substances.

Example 34 (Budesonide, Bead Gradient)

A batch of microspheres was made with budesonide, a small molecule drug which is not water soluble. This example demonstrates using the mixer to make microspheres with small molecule drugs as well as using a gradient of bead sizes to fine tune the particle size distribution. The median bead sizes of the gradient were 4 mm, 2 mm, 1 mm, and 0.327 mm.

An 10% w/w polymer-in-oil oil phase (Oil Phase) was prepared by dissolving 4.5 g grams of 50:50 poly(lactic-co-glycolic acid) (PLGA) (Resomer RG 504H, Lot number 10H40700512, Evonik Corp.) and 0.5 grams of budesonide (Sigma-Aldrich PHR1178-lot LRAA8997) in 44 grams of dichloromethane (DCM). A second phase, the Water Phase, was prepared by dissolving 2.67 grams of poly(vinyl alcohol) (PVA) in 267 grams of deionized water. The solution was stirred for one hour at 60° C. then stirred overnight at room temperature. A dilution water phase was made by setting the temperature of a vessel containing deionized water to 19° C. One of the three helical mixers was packed, from bottom to top, with 10.47 g of 4 mm borosilicate glass beads, 13.14 g of 2 mm borosilicate glass beads, 13.17 g of 1 mm borosilicate glass beads, and 71.6 g of 327 µm borosilicate glass beads (MO-SCI Health Care, GL0179B5/300-355) and 100 mesh screens (140 µm approximate retention) were placed on both the inlet and outlet.

The resulting Oil Phase and Water Phase were pumped simultaneously upwards, against gravity, through the bottom of the packed bed apparatus at rates of 9 ml/min and 21 ml/min, respectively. The sequential decrease of packing size through the helix enabled the gradual reduction of Reynolds number through the mixer. The 4 mm beads placed at the inlet of the mixer produced a laminar Reynolds number ranging from 0.58 to 10.25. The emulsion then flowed through the 2 mm and 1 mm packing producing a Reynolds number ranging from 0.28 to 5.12 followed a Reynolds number ranging from 0.15 to 2.56. The final particle size was produced as the emulsion flowed through the 327 µm packing, resulting in a final Reynolds number ranging from 0.05 to 0.84. The outgoing emulsion was met with the dilution water phase at a flowrate of 168 ml/min.

Once the remaining Oil Phase had been passed through the mixer, laser diffraction (Beckman Coulter LS 13 320) was used to analyze the particle size distribution of the resulting emulsion. The volumetric median particle size was found to be 47.22 µm with a d10 of 36.1 µm and d90 of 57.2 µm. The volume percent of particles in the desired range of 25-65 µm was 95.1%. The resulting microspheres were stirred at room temperature in a beaker to allow the methylene chloride to evaporate. After about 2 hrs, the microspheres were collected on a 25 µm screen and allowed to dry at room temperature. After drying, the microspheres were harvested from the screen. The total harvested mass was 1.8 grams of product.

The particle size distribution had a high percentage (95.1%) in the targeted range of 25-65 µm, which is slightly better than the previous examples, suggesting that the gradient of beads might help to fine tune the particle size distribution.

Example 35: (GLP-1, Double Emulsion, Bead Gradient)

A batch of microspheres was made with GLP-1 using an water/oil/water (w/o/w) emulsion. This example demonstrates using the mixer to make w/o/w microspheres with a water-soluble peptide as well as using a gradient of bead sizes to fine tune the particle size distribution. The median bead sizes of the gradient were 4 mm, 2 mm, 1 mm, and 0.327 mm.

A 10% w/w polymer-in-oil oil phase (Oil Phase) was prepared by dissolving 2.38 grams of 50:50 poly(lactic-co-glycolic acid) (PLGA) (Resomer RG 504H, Lot number 10H40700512, Evonik Corp.) in 22 grams of dichloromethane (DCM). Separately, 0.125 grams of GLP-1 (7-36) Chemleader (107444-51-9) was dissolved in 1.0 mL water. A second phase, the Water Phase, was prepared by dissolving 2.67 grams of poly(vinyl alcohol) (PVA) in 267 grams of deionized water. The solution was stirred for one hour at 60° C. then stirred overnight at room temperature. A dilution water phase was made by setting the temperature of a vessel containing deionized water to 19° C. One of the three helical mixers was packed, from bottom to top, with 10.47 g of 4 mm borosilicate glass beads, 13.14 g of 2 mm borosilicate glass beads, 13.17 g of 1 mm borosilicate glass beads, and 71.6 g of 327 μm borosilicate glass beads (MO-SCI Health Care, GL0179B5/300-355) and 100 mesh screens (140 μm approximate retention) were placed on both the inlet and outlet. The first emulsion (w/o) was made by adding the water/GLP-1 mixture to the PLGA/DCM mixture, followed by homogenization. The resulting w/o phase and the Water Phase were pumped simultaneously upwards, against gravity, through the bottom of the packed bed apparatus at rates of 9 ml/min and 21 ml/min, respectively.

The sequential decrease of packing size through the helix enabled the gradual reduction of Reynolds number through the mixer. The 4 mm beads placed at the inlet of the mixer produced a laminar Reynolds number ranging from 0.58 to 10.25. The emulsion then flowed through the 2 mm and 1 mm packing producing a Reynolds number ranging from 0.28 to 5.12 followed a Reynolds number ranging from 0.15 to 2.56. The final particle size was produced as the emulsion flowed through the 327 μm packing, resulting in a final Reynolds number ranging from 0.05 to 0.84. The outgoing emulsion was met with the dilution water phase at a flowrate of 168 ml/min.

Once the entirety of the w/o phase had been passed through the helical mixer, laser diffraction (Beckman Coulter LS 13 320) was used to analyze the particle size distribution of the resulting w/o/w emulsion. The volumetric median particle size was found to be 45.25 μm with a d10 of 33.55 μm and d90 of 55.37 μm. The volume percent of particles in the desired range of 25-65 μm was 94.4%. The resulting microspheres were stirred at room temperature in a beaker to allow the methylene chloride to evaporate. After about 2 hrs, the microspheres were collected on a 25 μm screen and allowed to dry at room temperature. After drying, the microspheres were harvested from the screen. The total harvested mass was 1.03 grams of product.

Example 36 (Albuterol Sulfate, Double Emulsion, Bead Gradient)

A batch of microspheres was made with albuterol sulfate using a water/oil/water (w/o/w) emulsion. Albuterol sulfate is a small molecule drug that is water soluble. This example demonstrates using the mixer to make w/o/w microspheres with a water-soluble small molecule drug, as well as using a gradient of bead sizes to fine tune the particle size distribution. The median bead sizes of the gradient were 4 mm, 2 mm, 1 mm, and 0.327 mm.

A 10% w/w polymer-in-oil oil phase (Oil Phase) was prepared by dissolving 2.38 grams of 50:50 poly(lactic-co-glycolic acid) (PLGA) (Resomer RG 504H, Lot number 10H40700512, Evonik Corp.) in 22 grams of dichloromethane (DCM). Separately, 0.125 grams of Buterol Sulfate (Sigma-Aldrich PHR1053-lot LRAA7128) was dissolved in 0.5 mL water. A second phase, the Water Phase, was prepared by dissolving 2.67 grams of poly(vinyl alcohol) (PVA) in 267 grams of deionized water. The solution was stirred for one hour at 60° C. then stirred overnight at room temperature. A dilution water phase was made by setting the temperature of a vessel containing deionized water to 19° C. One of the three helical mixers was packed, from bottom to top, with 10.47 g of 4 mm borosilicate glass beads, 13.14 g of 2 mm borosilicate glass beads, 13.17 g of 1 mm borosilicate glass beads, and 71.6 g of 327 μm borosilicate glass beads (MO-SCI Health Care, GL0179B5/300-355) and 100 mesh screens (140 μm approximate retention) were placed on both the inlet and outlet. The first emulsion (w/o) was made by adding the water/Buterol Sulfate mixture to the PLGA/DCM mixture, followed by homogenization. The resulting w/o phase and the Water Phase were pumped simultaneously upwards, against gravity, through the packed bed apparatus at rates of 9 ml/min and 21 ml/min, respectively.

The sequential decrease of packing size through the helix enabled the gradual reduction of Reynolds number through the mixer. The 4 mm beads placed at the inlet of the mixer produced a laminar Reynolds number ranging from 0.58 to 10.25. The emulsion then flowed through the 2 mm and 1 mm packing producing a Reynolds number ranging from 0.28 to 5.12 followed a Reynolds number ranging from 0.15 to 2.56. The final particle size was produced as the emulsion flowed through the 327 μm packing, resulting in a final Reynolds number ranging from 0.05 to 0.84. The outgoing emulsion was met with the dilution water phase at a flowrate of 168 ml/min.

Once the entirety of the w/o phase had been passed through the mixer, laser diffraction (Beckman Coulter LS 13 320) was used to analyze the particle size distribution of the resulting emulsion. The volumetric median particle size was found to be 47.54 μm with a d10 of 25.76 μm and d90 of 59.49 μm. The volume percent of particles in the desired range of 25-65 μm was 88.3%. The resulting microspheres were stirred at room temperature in a beaker to allow the methylene chloride to evaporate. After about 2 hrs, the microspheres were collected on a 25 μm screen and allowed to dry at room temperature. After drying, the microspheres were harvested from the screen. The total harvested mass was 1.18 grams of product.

Example 37 (Two Different Microspheres)

Two different oil phases were prepared. The first 15% w/v polymer-in-oil phase (Oil Phase) was prepared by combining 0.255 grams of 50:50 poly(D,L-lactide-co-glycolide) (PLGA) (Resomer RG 502H, Lot number LP1487, Evonik Corp.) and 0.045 grams of a 5K PEGylated insulin in a solution of 2 mL dichloromethane (DCM) and 18 microliters of 50 mg/ml pamoic acid prepared in N-Dimethylformamide (DMF). This oil phase was then allowed to stir at room temperature (~19° C.) until completely dissolved. A second 10% w/v polymer-in-oil phase (Oil Phase) was prepared by combining 0.170 grams of 50:50 poly(D,L-lactide-co-glycolide) (PLGA) (Resomer RG 502, Lot number D140800505, Evonik Corp.) and 0.030 grams of a 5K PEGylated GLP-1 in a solution of 1.75 mL of dichloromethane (DCM), 250 microliters of benzyl alcohol, and 18 microliters of 50 mg/ml pamoic acid prepared in N-Dimethylformamide (DMF). This second oil phase was then allowed to stir at room temperature (~19° C.) until completely dissolved. A Water Phase was made by dissolving 10 grams of poly(vinyl alcohol) (PVA) in 1000 milliliters of deionized water. Five milliliters of the PVA solution was added to each oil phase and the oil phases were stirred to form course emulsions.

The two course emulsions were pumped through two separate helical mixers at 3.8 ml/min and microspheres were collected together in 400 milliliters of a 20% w/v sucrose solution stirring at 120 rpm. The resulting Reynolds number through the two helices was laminar, falling between 0.07 and 0.13. After 1 hour, the microspheres were centrifuged at 33 g for 5 minutes and washed three times with Milli-Q water. The particle size distribution of the microspheres was analyzed using laser diffraction (Beckman Coulter LS 13 320). The volumetric median particle size of the microspheres was 37.6 µm with a d10 of 27.3 µm and a d90 of 46.3 µm.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

In the preceding description, for the purposes of explanation, numerous details have been set forth in order to provide an understanding of various embodiments of the present technology. It will be apparent to one skilled in the art, however, that certain embodiments may be practiced without some of these details, or with additional details.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Additionally, details of any specific embodiment may not always be present in variations of that embodiment or may be added to other embodiments.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a method" includes a plurality of such methods and reference to "the tube" includes reference to one or more tubes and equivalents thereof known to those skilled in the art, and so forth. The invention has now been described in detail for the purposes of clarity and understanding. However, it will be appreciated that certain changes and modifications may be practice within the scope of the appended claims.

All publications, patents, and patent applications cited herein are hereby incorporated by reference in their entirety for all purposes. None is admitted to be prior art.

What is claimed is:

1. A system for forming an emulsion, the system including:
   a coiled tube, wherein:
      the coiled tube comprises a first end and a second end, and
      the second end is disposed at a position higher than the position of the first end;
   a plurality of beads disposed within the coiled tube;
   a first inlet fluidly connected to the coiled tube, wherein the first inlet is configured to deliver a first fluid to the first end before the second end;
   a second inlet fluidly connected to the coiled tube, wherein the second inlet is configured to deliver a second fluid to the first end before the second end; and
   a plurality of screens configured to remove wastewater and fines and aggregates, wherein:
      the coiled tube is fluidly connected to the plurality of screens, and
      the plurality of screens is in closer fluid communication with the second end than the first end.

2. The system of claim 1, further comprising a pump fluidly connected to the coiled tube configured to drive a flow of fluid from the first end to the second end.

3. The system of claim 1, further comprising a device for applying pressure to a fluid to drive a flow of the fluid from the first end to the second end.

4. The system of claim 1, wherein the coiled tube is characterized by a helix angle ranging from 0 to 90 degrees.

5. The system of claim 1, further comprising a third inlet fluidly connected to the coiled tube, wherein the third inlet is in closer fluid communication with the second end than the first end.

6. The system of claim 1, wherein the plurality of beads is characterized by a median diameter within a range of 1 µm to 4 mm.

7. The system of claim 1, wherein:
   the coiled tube is a first coiled tube,
   the first coiled tube is coiled around a longitudinal axis, and
   the first coiled tube is characterized by a first width in a direction perpendicular to the longitudinal axis,
   the system further comprising:
   a second coiled tube, wherein:
      the second coiled tube comprises a second plurality of beads disposed therein,
      the second coiled tube is coaxial with the longitudinal axis,
      the second coiled tube is characterized by a second width in a direction perpendicular to the longitudinal axis, wherein:
   the first coiled tube and the second coiled tube are arranged such that a pair of the first coiled tube and the second coiled tube is characterized by a third width perpendicular to the longitudinal axis,
   the third width is equal to the first width and to the second width.

8. The system of claim 7, wherein the system comprises a third coiled tube.

9. The system of claim 1, wherein:
the coiled tube is coiled around a longitudinal axis, and the longitudinal axis is vertical.

10. A system for forming an emulsion, the system including:
a plurality of coiled tubes, wherein for each coiled tube of the plurality of coiled tubes:
the coiled tube comprises a first end and a second end,
the second end is disposed at a position higher than the position of the first end,
a first inlet is fluidly connected to the coiled tube, wherein the first inlet is configured to deliver a first fluid to the first end before the second end,
a second inlet is fluidly connected to the coiled tube, wherein the second inlet is configured to deliver a second fluid to the first end before the second end,
a plurality of beads is disposed within the coiled tube,
the coiled tube is coiled around a longitudinal axis,
the coiled tube is characterized by a first width in a direction perpendicular to the longitudinal axis;
wherein:
the plurality of coiled tubes are coaxial with the longitudinal axis,
the plurality of coiled tubes is characterized by a second width in the direction perpendicular to the longitudinal axis, and
the first width is equal to the second width.

11. The system of claim 10, wherein:
each coiled tube of the plurality of coiled tubes is characterized by a first height in the direction of the longitudinal axis,
the plurality of coiled tubes is characterized by a second height in the direction of the longitudinal axis, and
the first height is equal to the second height.

12. The system of claim 10, wherein the plurality of beads comprises:
a first portion of the plurality of beads having a first median diameter,
a second portion of the plurality of beads having a second median diameter,
wherein:
the first median diameter is statistically different from the second median diameter, and
the second portion is disposed higher than the first portion in each coiled tube of the plurality of coiled tubes.

13. The system of claim 12, wherein the plurality of beads further comprises:
a third portion of the plurality of beads having a third median diameter,
wherein:
the third median diameter is statistically different from the first median diameter and the second median diameter,
the third portion is disposed higher than the first portion, and
the first median diameter, the second median diameter, and the third median diameter monotonically increase or monotonically decrease from the first end to the second end.

14. The system of claim 10, further comprising a pump fluidly connected to the plurality of coiled tubes configured to drive a flow of fluid from the first end to the second end of each coiled tube of the plurality of coiled tubes.

15. The system of claim 10, further comprising a device for applying pressure to a fluid to drive a flow of the fluid from the first end to the second end of each coiled tube of the plurality of coiled tubes.

16. The system of claim 10, wherein each coiled tube of the plurality of coiled tubes is characterized by a helix angle ranging from 0 to 90 degrees.

17. The system of claim 10, wherein for each coiled tube of the plurality of coiled tubes:
a third inlet is fluidly connected to the coiled tube, wherein the third inlet is in closer fluid communication with the second end than the first end.

18. The system of claim 10, further comprising:
a plurality of screens configured to remove wastewater and fines and aggregates, wherein:
each coiled tube of the plurality of coiled tubes is fluidly connected to the plurality of screens, and
for each coiled tube of the plurality of coiled tubes:
the plurality of screens is in closer fluid communication with the second end than the first end.

19. The system of claim 10, wherein the plurality of beads is characterized by a median diameter within a range of 1 μm to 4 mm.

20. The system of claim 10, wherein for each coiled tube of the plurality of coiled tubes:
the coiled tube is coiled around a longitudinal axis, and the longitudinal axis is vertical.

21. The system of claim 10, wherein the plurality of coiled tubes comprises three coiled tubes.

22. A system for forming an emulsion, the system including:
a first coiled tube, wherein:
the first coiled tube comprises a first end and a second end,
the second end is disposed at a position higher than the position of the first end,
the first coiled tube is coiled around a longitudinal axis, and
the first coiled tube is characterized by a first width in a direction perpendicular to the longitudinal axis;
a first plurality of beads disposed within the first coiled tube;
a first inlet fluidly connected to the first coiled tube, wherein the first inlet is configured to deliver a first fluid to the first end before the second end;
a second inlet fluidly connected to the first coiled tube, wherein the second inlet is configured to deliver a second fluid to the first end before the second end; and
a second coiled tube, wherein:
the second coiled tube comprises a second plurality of beads disposed therein,
the second coiled tube is coaxial with the longitudinal axis,
the second coiled tube is characterized by a second width in a direction perpendicular to the longitudinal axis,
the first coiled tube and the second coiled tube are arranged such that a pair of the first coiled tube and the second coiled tube is characterized by a third width perpendicular to the longitudinal axis, and
the third width is equal to the first width and to the second width.

23. The system of claim 22, wherein the system comprises a third coiled tube.

24. The system of claim 22, further comprising a pump fluidly connected to the first coiled tube configured to drive a flow of fluid from the first end to the second end.

25. The system of claim 22, further comprising a device for applying pressure to a fluid to drive a flow of the fluid from the first end to the second end of the first coiled tube.

26. The system of claim 22, wherein the first coiled tube and the second coiled tube are each characterized by a helix angle ranging from 0 to 90 degrees.

27. The system of claim 22, further comprising a third inlet fluidly connected to the first coiled tube, wherein the third inlet is in closer fluid communication with the second end than the first end.

28. The system of claim 22, further comprising:
a plurality of screens configured to remove wastewater and fines and aggregates, wherein:
the first coiled tube and the second coiled tube are fluidly connected to the plurality of screens, and
the plurality of screens is in closer fluid communication with the second end than the first end.

29. The system of claim 22, wherein the first plurality of beads and the second plurality of beads are characterized by a median diameter within a range of 1 μm to 4 mm.

30. The system of claim 22, wherein:
the first coiled tube is coiled around a longitudinal axis,
the second coiled tube is coiled around the longitudinal axis, and
the longitudinal axis is vertical.

* * * * *